United States Patent [19]

Berges

[11] 4,220,644
[45] Sep. 2, 1980

[54] 7-ACYLAMINO-3-(SUBSTITUTED TETRAZOLYL THIOMETHYL) CEPHALOSPORINS

[75] Inventor: David A. Berges, Wayne, Pa.

[73] Assignee: SMITHKLINE Smithkline Corporation, Philadelphia, Pa.

[21] Appl. No.: 682,805

[22] Filed: May 3, 1976

Related U.S. Application Data

[63] Continuation-in-part of Ser. No. 536,760, Dec. 27, 1974.

[51] Int. Cl.² ............... A61K 31/545; C07D 501/36
[52] U.S. Cl. .................................. 424/246; 544/21; 544/26; 544/27; 548/253
[58] Field of Search ............... 260/243 C; 424/246; 544/26, 27, 21

[56] References Cited

U.S. PATENT DOCUMENTS

| | | | |
|---|---|---|---|
| 3,516,997 | 6/1970 | Takano et al. | 260/243 C |
| 3,819,623 | 6/1974 | Takano et al. | 544/27 |
| 3,855,213 | 12/1974 | Dunn et al. | 544/26 |
| 3,989,694 | 11/1976 | Berges | 544/27 |
| 4,018,921 | 4/1977 | Gleason | 544/26 |
| 4,034,092 | 7/1977 | Berges | 544/27 |
| 4,100,346 | 7/1978 | Gottstein et al. | 544/27 |
| 4,113,944 | 9/1978 | Kai et al. | 544/27 |
| 4,118,563 | 10/1978 | Lim et al. | 544/26 |
| 4,126,682 | 11/1978 | Berges | 544/27 |
| 4,142,046 | 2/1979 | Berges | 544/27 |
| 4,145,418 | 3/1979 | Kuwada et al. | 544/27 |

FOREIGN PATENT DOCUMENTS

| | | |
|---|---|---|
| 814546 | 4/1974 | Belgium . |
| 2442702 | 3/1975 | Fed. Rep. of Germany . |
| 2170496 | 10/1973 | France . |

*Primary Examiner*—Donald G. Daus
*Assistant Examiner*—David E. Wheeler
*Attorney, Agent, or Firm*—Janice E. Williams; Alan D. Lourie

[57] ABSTRACT

The compounds of this invention are cephalosporins having various acyl substituents at the 7-position and a substituted tetrazolyl thiomethyl group at the 3-position of the cephem nucleus and intermediates for the preparation thereof. The 7-acylated compounds have antibacterial activity.

21 Claims, No Drawings

7-ACYLAMINO-3-(SUBSTITUTED TETRAZOLYL THIOMETHYL) CEPHALOSPORINS

This application is a continuation-in-part of copending U.S. application Ser. No. 536,760 filed Dec. 27, 1974.

This invention comprises a new series of cephalosporin compounds which have antibacterial activity when administered either orally or parenterally and to intermediates for the preparation thereof. In particular, the structures of the biologically active cephalosporin compounds of this invention are characterized by having a novelly substituted tetrazolyl thiomethyl group at the 3-position of the cephem nucleus. Also, this invention extends to methods and compositions for treating certain bacterial infections using these new compounds as well as to certain chemical intermediates and methods for preparing the compounds described hereafter.

The compounds of this invention are represented by the following structural formula:

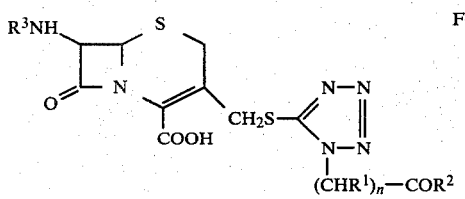

FORMULA I in which:
each individual $R^1$ is hydrogen or lower alkyl;
n is one to ten;
$R^2$ is hydroxy, amino, lower alkylamino or di(lower)alkylamino; and
$R^3$ is an acyl group selected from the group consisting of:

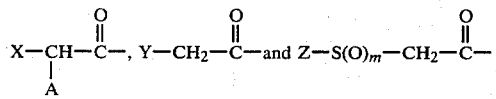

where:
X is thienyl; dihydrophenyl; phenyl; phenyl monosubstituted with hydroxy, hydroxymethyl, formamido, ureido or carboxymethylamino; or 3-fluoro-4-hydroxyphenyl;
A is $NH_2$, OH, COOH or $SO_3H$;
Y is cyano, sydnone or aminomethylphenyl;
Z is methyl, trifluoromethyl, trifluoroethyl or pyridyl; and
m is zero to two, or a non-toxic pharmaceutically acceptable salt thereof.

As used herein, the term "lower alkyl" refers to groups having from one to four carbon atoms.

It will be recognized that the 4-carboxylic acid group of the compounds of Formula I may be readily esterified by methods well known to the art. These esters include, for example, simple alkyl and aryl esters as well as esters which are easily cleaved, within the body, to the parent acid such as indanyl, pivaloyloxymethyl, acetoxymethyl, propionyloxymethyl, glycyloxymethyl, phenylglycyloxymethyl and thienylglycyloxymethyl esters and others. Of course, when A is COOH, this group may be similarly esterified. All such esters are included within the scope of this invention.

Preferred compounds of this invention are represented by Formula I where $R^1$ is hydrogen; n is one to five; $R^2$ is hydroxy, amino, lower alkylamino or di(lower)alkylamino; $R^3$ is

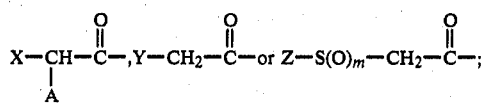

X is thienyl, dihydrophenyl, phenyl, phenyl mono-substituted with hydroxy, hydroxymethyl, formamido, ureido, carboxymethylamino, or 3-fluoro-4-hydroxyphenyl; A is $NH_2$, OH, COOH or $SO_3H$; Y is cyano, sydnone or aminomethylphenyl; Z is methyl, trifluoromethyl, trifluoroethyl or pyridyl and m is zero to two.

Advantageous compounds of this invention are represented by Formula I where $R^1$ is hydrogen; n is one to five; $R^2$ is hydroxy, amino, lower alkylamino or di(lower)alkylamino; $R^3$ is

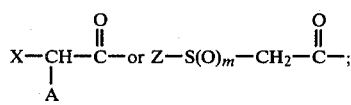

X is phenyl or hydroxyphenyl; A is $NH_2$ or OH; Z is methyl, trifluoromethyl or trifluoroethyl and m is zero to two.

Most advantageous are the compounds represented by Formula I where $R^1$ is hydrogen; n is one to five; $R^2$ is hydroxy or amino; $R^3$ is

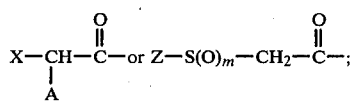

X is phenyl or 4-hydroxyphenyl; A is $NH_2$ or OH; Z is trifluoromethyl and m is zero.

Examples of the most preferred 7-acyl substituents ($R^3NH-$) of the compounds of Formula I are listed below:
α-hydroxyphenylacetamido
α-aminophenylacetamido
α-amino-4-hydroxyphenylacetamido
trifluoromethylmercaptoacetamido
methylmercaptoacetamido
2,2,2-trifluoroethylsulfinylacetamido
cyanoacetamido
α-carboxythienylacetamido
α-carboxyphenylacetamido
α-sulphophenylacetamido
methylsulfonylacetamido
α-amino-4-carboxymethylaminophenylacetamido
α-amino-3-fluoro-4-hydroxyphenylacetamido
3-sydnoneacetamido
4-pyridylthioacetamido
2-aminomethylphenylacetamido.

Most preferred substituted tetrazolyl groups are the following:
1-carboxymethyltetrazolyl
1-carbamoylmethyltetrazolyl
1-(2-carboxyethyl)tetrazolyl
1-(2-carbamoylethyl)tetrazolyl
1-(3-carboxypropyl)tetrazolyl
1-(3-carbamoylpropyl)tetrazolyl 1-(4-carboxybutyl)tetrazolyl
1-(4-carbamoylbutyl)tetrazolyl
1-(5-carboxypentyl)tetrazolyl
1-(5-carbamoylpentyl)tetrazolyl.

Particularly preferred are the compounds 7-D-mandelamido-3-(1-carboxymethyltetrazol-5-ylthiomethyl)-3-cephem-4-carboxylic acid, 7-D-mandelamido-3-(1-carbamoylmethyltetrazol-5-ylthiomethyl)-3-cephem-4-carboxylic acid, 7-D-mandelamido-3-[1-(2-carbamoylethyl)tetrazol-5-ylthiomethyl]-3-cephem-4-carboxylic acid, 7-D-mandelamido-3-[1-(2-carboxyethyl)tetrazol-5-ylthiomethyl]-3-cephem-4-carboxylic acid, 7-D-mandelamido-3-[1-(3-carbamoylpropyl)tetrazol-5-ylthiomethyl]-3-cephem-4-carboxylic acid, 7-D-mandelamido-3-[1-(3-carboxypropyl)tetrazol-5-ylthiomethyl]-3-cephem-4-carboxylic acid, 7-D-mandelamido-3-[1-(5-carboxypentyl)tetrazol-5-ylthiomethyl]-3-cephem-4-carboxylic acid, 7-D-mandelamido-3-[1-(5-carbamoylpentyl)tetrazol-5-ylthiomethyl]-3-cephem-4-carboxylic acid, 7-(D-α-amino-4-hydroxyphenylacetamido)-3-(1-carboxymethyltetrazol-5-ylthiomethyl)-3-cephem-4-carboxylic acid, 7-(D-α-amino-4-hydroxyphenylacetamido)-3-(1-carbamoylmethyltetrazol-5-ylthiomethyl)-3-cephem-4-carboxylic acid, 7-trifluoromethylmercaptoacetamido-3-(1-carbamoylmethyltetrazol-5-ylthiomethyl)-3-cephem-4-carboxylic acid, 7-trifluoromethylmercaptoacetamido-3-[1-(2-carbamoylethyl)tetrazol-5-ylthiomethyl]-3-cephem-4-carboxylic acid, 7-trifluoromethylmercaptoacetamido-3-(1-carboxymethyltetrazol-5-ylthiomethyl)-3-cephem-4-carboxylic acid, 7-trifluoromethylmercaptoacetamido-3-[1-(2-carboxyethyl)tetrazol-5-ylthiomethyl]-3-cephem-4-carboxylic acid and 7-trifluoromethylmercaptoacetamido-3-[1-(3-carbamoylpropyl)tetrazol-5-ylthiomethyl]-3-cephem-4-carboxylic acid.

Cephalosporin derivatives having 7-acyl substituents as defined above are all documented in the prior art. Substitution by a substituted S-heterocyclicthiomethyl group (—CH$_2$SHet) at the 3-position of the cephem nucleus is also known and is disclosed in Netherlands Pat. No. 6916151 where Het is, among others, tetrazolyl substituted with, inter alia, carboxy, carbalkoxy, alkoxyalkylaminocarbonyl and dialkylaminoalkylaminocarbonyl and in Japanese Pat. No. 7205550 where Het includes tetrazolyl substituted with —(CH$_2$)$_n$R$^3$ where n is 0 to 3 and R$^3$ includes alkoxycarbonyl, carboxy, N-alkoxyalkylcarbamoyl and dialkylamino. The compounds disclosed in Netherlands Pat. No. 6916151, however, have a similarly substituted heterocyclic acetamido group at the 7-position, while those of Japanese Pat. No. 7205550 contain a 7-thienylacetamido or 7-tetrazolylacetamido group. Recently issued U.S. Pat. No. 3,819,623 discloses but does not claim cephalosporins bearing a 7-heterocyclicacetamido or 7-heterocyclicthioalkylacetamido group and having in the 3-position, inter alia, thiomethyltetrazolyl substituted with carboxy, alkoxycarbonyl, carboxyalkyl, alkoxycarbonylalkyl and dialkylaminoalkylaminocarbonylalkyl. No compounds containing both applicant's 7-acyl groups and the 3-substituted tetrazolylthiomethyl moiety disclosed herein are believed to be known to the art.

The compounds of Formula I are prepared by acylation of an appropriate 7-amino-3-substituted tetrazolylthiomethyl cephalosporin nucleus of Formula II:

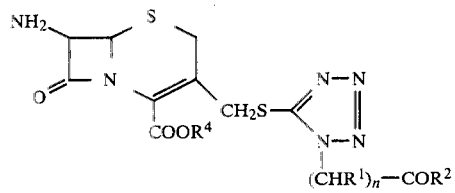

FORMULA II in which:
each individual R$^1$ is hydrogen or lower alkyl;
n is one to ten;
R$^2$ is hydroxy, amino, lower alkylamino or di(lower)alkylamino; and
R$^4$ is hydrogen or a protecting ester group,
with an appropriate acylating agent followed by removal of the protective groups when present. The carboxylic acid group of the acylating agent is activated by any of the standard methods such as conversion to the mixed anhydride, acid chloride or activated ester. In addition, a reagent such as dicyclohexylcarbodiimide or carbonyldiimidazole can be used provided that the carboxyl group on the cephem nucleus is protected with an easily removable protecting group such as a benzhydryl, t-butyl, trichloroethyl, benzyl, benzyloxymethyl, p-nitrophenyl, p-methoxyphenyl, p-methoxybenzyl or p-nitrobenzyl ester. When A is NH$_2$, the α-amino group of the acylating agent is, preferably, protected prior to acylation with an easily removable protective group known in the art such as t-butoxycarbonyl, trichloroethoxycarbonyl, benzyloxycarbonyl, the methyl acetoacetate adduct or similar groups commonly used in the synthesis of peptides. The compounds represented by Formula II above are also considered as objects of this invention.

Alternatively, the compounds of Formula I are prepared by acylating 7-aminocephalosporanic acid with an appropriately protected acylating agent, as described above, and then displacing the 3-acetoxy group with the desired substituted tetrazole thiol with subsequent removal of the protective group(s). The substituted tetrazole thiols of the formula:

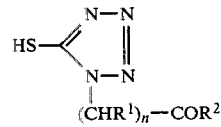

FORMULA III in which:
each individual R$^1$ is hydrogen or lower alkyl;
n is one to ten; and
R$^2$ is hydroxy, amino, lower alkylamino or di(lower)alkylamino,
are also objects of this invention.

The protective groups can be removed according to methods well known to the art, such as with trifluoroacetic acid when t-butyl or t-butoxycarbonyl protective groups are used. The resulting salt is converted to the zwitterionic product or to the free acid by means of a basic ion exchange resin such as polystyrene-amine ion exchange resin (Amberlite IR-45) or else by basification of an aqueous solution of the salt.

The acylating agents used as starting materials are either known or prepared by known methods.

The 7-amino-3-substituted tetrazolylthiomethyl cephalosporin starting materials of Formula II are prepared from reaction of 7-aminocephalosporanic acid and a substituted tetrazole thiol of Formula III.

The substituted tetrazole thiols of Formula III where $R^2$ is hydroxy are prepared by reaction of an isothiocyanate, for example ethyl isothiocyanoacetate, or an N-alkyl dithiocarbamate, such as methyl 2-carboxyethyldithiocarbamate, with an azide such as sodium azide. When $R^2$ is amino, lower alkylamino or di(lower)alkylamino, the tetrazole thiols of Formula III are prepared from the corresponding tetrazole thiols where $R^2$ is hydroxy by standard methods for the preparation of amides from acids, for example, by reaction of a tetrazole thiol where $R^2$ is hydroxy with 1,1-carbonyldiimidazole and an amine of the formula $NHR^5R^6$ where $R^5$ and $R^6$ are each hydrogen or lower alkyl, or by conversion of the tetrazole thiol where $R^2$ is hydroxy to the corresponding acid chloride with subsequent reaction of the acid chloride with an amine ($NHR^5R^6$). The tetrazole thiols of Formula III are also prepared by conversion of a suitably substituted hydroxy tetrazole to the corresponding thiol by the method of Hoover and Day [*J. Amer. Chem. Soc.* 78:5832 (1956)].

The compounds of this invention are capable of forming salts with, for example, the alkali metals such as sodium or potassium, the alkaline earth metals such as calcium or with the ammonium cation. When A is $NH_2$, the compounds can exist as the zwitterion or as an acid or base salt. These salts are prepared by standard methods using a wide variety of non-toxic pharmaceutically acceptable acids and bases known in the art and are also considered as objects of this invention.

It will be recognized that due to the asymmetric α-carbon atom in the 7-acetamido group of Formula I when $R^3$ is

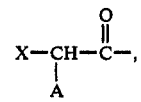

optical isomers will exist. Racemic or resolved products are obtained depending upon whether a racemic or resolved side chain acid is used as an acylating agent. The resolved side chain acids are readily obtained from the racemic compounds by resolution according to well known methods, including fractional crystallization of a salt formed with an optically active acid or base. All of the isomers, including separated isomers and mixtures thereof, are included within the scope of this invention.

The compounds of Formula I have antibacterial activity against both Gram-positive and Gram-negative organisms. Minimum inhibitory concentrations (MIC's) ranged from 0.2 to >200 μg./ml. in in vitro testing. These results are shown in Table 1 below for representative compounds of Formula I. In vivo mouse protection data are given in Table 2. Compound names corresponding to numbers are given in the experimental section. For comparative purposes, data for cephamandole, which is 7-mandelamido-3-(1-methyltetrazol-5-ylthiomethyl)-3-cephem-4-carboxylic acid, is also given in Tables 1 and 2.

TABLE 1

| Compound | S. aureus HH 127 | S. aureus SK 23390 | S. villaluz | Strep. Faecalis HH 34358 | E. coli SK 12140 | E. coli HH 33779 | Kleb. pneumo. SK 4200 | Kleb. pneumo. SK 1200 | Pseudo. sp. HH 63 | Salmonella ATCC 12176 | Shigella HH 117 | Entero. aerog. ATCC 13048 | Serra. Marc. ATCC 13880 | Entero. cloacae HH 31254 | Proteus morgani 179 |
|---|---|---|---|---|---|---|---|---|---|---|---|---|---|---|---|
| I | 6.3 | 3.1, 1.6 | 100 | 100 | 1.6 | 1.6, 6.3 | 1.6, 0.8 | 1.6, 0.8 | >200 | 1.6, 0.8 | 1.6, 0.8 | 6.3, 12.5 | 100, 25 | 0.8 | 3.1 |
| II | 12.5 | 12.5 | 200 | 100 | 3.1 | 12.5 | 1.6 | 6.3 | >200 | 1.6 | 6.3 | 25 | >200 | 1.6 | >200 |
| III | 1.6 | 3.1 | 25 | 25 | 3.1 | 3.1 | 3.1 | 3.1 | >200 | 0.8 | 3.1 | 3.1 | 25 | 3.1 | 3.1 |
| IV | 1.6 | 0.8 | 50 | 25 | 3.1 | 6.3 | 3.1 | 1.6 | >200 | 0.8 | 0.8 | 6.3 | 100 | 1.6 | 1.6 |
| V | 1.6 | 3.1, 1.6 | 25 | 25 | 0.8 | 1.6 | 1.6 | 0.8, 0.4 | >200 | 0.8, 0.4 | 0.2, 0.4 | 1.6 | 12.5 | 0.8, 0.4 | 1.6, 3.1 |
| VI | 6.3 | 6.3 | 50 | 50 | 6.3 | 6.3 | 12.5 | 6.3 | >200 | 1.6 | 3.1 | 6.3 | 100 | 3.1 | 50 |
| VII | 3.1 | 0.8 | 6.3 | 12.5 | 0.4 | 1.6 | 0.8 | 0.4 | >200 | 0.2 | 0.2 | 1.6 | 6.3 | 0.4 | 1.6 |
| | 1.6 | 0.4 | 6.3 | 12.5 | 0.4 | 1.6 | 0.4 | 0.2 | >200 | 0.2 | 0.2 | 0.8 | 6.3 | 1.6 | 0.8 |
| | 0.8 | 0.4 | 1.6 | 25 | 0.8 | 3.1, 1.6 | 0.8 | 0.8 | >200 | 0.8 | 0.4 | 6.3 | 50 | 0.8 | 1.6 |
| VIII | 3.1, 1.6 | 0.2, 1.6 | 50, 3.1 | 50, 100 | 0.4, 1.6 | 1.6, 6.3 | 1.6 | 0.4, 1.6 | >200 | 0.8, 0.4 | 0.8, 0.8 | 3.1, 6.3 | 50, 100 | 6.3, 3.1 | 3.1, 6.3, 1.6 |
| IX | 12.5 | 6.3 | 100 | 25 | 12.5 | 12.5 | 6.3 | 6.3 | >200 | 3.1 | 6.3 | 12.5 | 200 | 0.8 | 100 |
| X | 6.3 | 12.5 | 25 | 25 | 1.6 | 1.6 | 1.6 | 3.1 | >200 | 0.8 | 1.6 | 3.1 | 25 | 1.6 | 25 |
| XI | 3.1 | 3.1 | 50 | 50 | 0.4 | 3.1 | 0.8 | 0.8 | >200 | 0.8 | 0.4 | 3.1 | 25 | 3.1 | 0.8 |
| XII | 3.1 | 0.4 | 12.5 | 12.5 | 1.6 | 1.6 | 1.6 | 0.8, 1.6 | >200 | 0.4, 0.8 | 0.4 | 3.1 | 12.5 | 0.8 | 1.6 |
| XIII | 3.1 | 0.8 | 12.5 | 25 | 1.6 | 3.1 | 0.8 | 1.6 | >200 | 1.6 | 0.8 | 6.3 | 12.5 | 0.8 | 1.6 |
| XIV | 1.6 | 0.4 | 6.3 | 12.5 | 3.1 | 3.1 | 1.6 | 3.1 | >200 | 3.1 | 0.8 | 6.3 | 25 | 1.6 | 1.6 |
| XV | 1.6 | 0.8 | 25 | 50 | 0.8 | 3.1 | 0.8 | 0.4 | — | 0.4 | 0.2 | 6.3 | 200 | 0.8 | >200 |
| XVI | 0.4 | 0.8 | 6.3 | 12.5 | 0.4 | 1.6 | 0.8 | 0.4 | >200 | 0.4 | 0.2 | 1.6 | 12.5 | 0.4 | 12.5 |
| XVII | 0.4 | 0.4 | 12.5 | 25 | 0.4 | 3.1 | 0.8 | 0.4 | — | 0.4 | 0.2 | 1.6 | 100 | 0.8 | 200 |
| XVIII | 3 | 3 | 100 | 100 | 0.8 | 6 | 0.4 | 6 | — | 0.8 | 3 | 13 | >200 | 3 | 200 |
| XIX | 50 | 50 | 100 | 200 | 25 | 50 | 50 | — | >200 | 25 | 6 | 50 | 50 | 50 | 6 |
| XX | 0.4 | 0.2 | 3.1 | 6.3 | 0.8 | 0.8 | 0.4 | 0.4 | >200 | 0.2 | 0.2 | 3.1 | 12.5 | 0.8 | 12.5 |
| cephamandole | 1.0 | 0.6 | 8 | 2.3 | 1.1 | 2.6 | 1.1 | 0.6 | >200 | 0.6 | 0.2 | 2.9 | 13 | 0.7 | 1.3 |

TABLE 2

| | ED$_{50}$ in vivo. (mg./kg.) | | | |
|---|---|---|---|---|
| | E. coli 12140 | | Kleb. pneumo. 4200 | |
| Compound | s.c. | p.o. | s.c. | p.o. |
| I | 1.56 | 50 | <0.78 | 0.14 25 |
| II | 0.86,1.56, 5.5 | 98>200, 200 | <0.78 | 0.26 13.2,15.5 |
| III | 1.56 | 34 | 2.8 | >50 |
| IV | 2.5 | 168 | 7.5 | 168 |
| V | 1.56 | 50 | 1.3 | 21.2 |
| VI | <0.2,1.56 | 3,6.25 | 0.92 | 4 |
| VII | 0.86 | 25 | 0.78 | 17 |
| VIII | 0.86 | 50 | 0.46 | 25 |
| IX | 1.56 | 28.5 | 3.7 | 18 |
| X | 0.78 | 25 | 0.62 | 15.6,18.2 |
| XI | 1.56 | >50 | 0.37 | 25 |
| XII | 1.84 | >50 | 2.9 | — |
| XIII | 1.56 | — | 0.54 | — |
| XIV | 1.1 | — | 1.1 | — |
| XV | 1.56 | >50 | 1.12 | 46 |
| XVI | 0.78 | 25 | 0.54 | — |
| XVII | 0.28 | 6.25 | 0.78 | 15.5 |
| XVIII | 3.1 | — | 0.4 | — |
| XIX | — | — | — | — |
| XX | 0.70 | 21.5 | — | — |
| cephamandole | <2,2 | 28 | 0.96 | >50,50 |

In addition, the active compounds of this invention exhibit broad spectrum activity and show advantageously high blood serum levels and half-life values. It is also pointed out that the compounds of Formula I were A is OH and X is phenyl are especially active against Serratia, Enterobacter and indole positive Proteus bacteria.

Pharmaceutical compositions having antibacterial activity which comprise a pharmaceutical carrier containing an active but non-toxic quantity of a compound of Formula I as well as methods of combatting bacterial infections by administering such a composition to an infected host in a nontoxic amount sufficient to combat such infections are also objects of this invention. The administration may be orally or by parenteral injection such as subcutaneously, intramuscularly or intravenously. The injection of suitably prepared sterile solutions or suspensions containing an effective, nontoxic amount of the new cephalosporin compound is the preferred route of administration.

The compounds of Formula I are formulated and administered in the same manner as other cephalosporins. The dosage regimen comprises administration, preferably by injection, of an active but nontoxic quantity of a compound of Formula I selected from the dosage unit range of from 100 to 1000 mg. with the total daily dosage regimen being from 400 mg. to 6 g. The precise dosages are dependent upon the age and weight of the subject and on the infection being treated and can be determined by those skilled in the art based on the data disclosed herein compared with that available to the art attained with known cephalosporins.

Also considered within the scope of this invention are the 7α-methoxy analogs of the compounds of Formula I, which compounds are represented by the following structural formula:

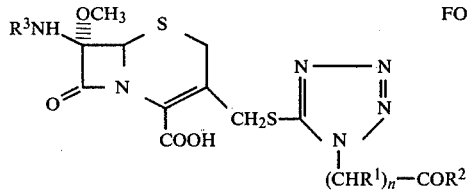

FORMULA IV or a non-toxic pharmaceutically acceptable salt thereof, in which $R^1$, $R^2$, $R^3$ and n are as previously defined hereabove.

A selected group of the compounds of Formula IV are those where $R^1$ is hydrogen and n is one to five.

Representative of the compounds of Formula IV are 7β-D-mandelamido-7-α-methoxy-3-[1-(2-carboxyethyl)tetrazol-5-ylthiomethyl]-3-cephem-4-carboxylic acid, 7-β-cyanoacetamido-7-α-methoxy-3-[1-(2-carboxyethyl)tetrazol-5-ylthiomethyl]-3-cephem -4-carboxylic acid, 7β-(D-α-aminophenylacetamido)-7α-methoxy -3-[1-(2-carboxyethyl)tetrazol-5-ylthiomethyl]-3-cephem-4-carboxylic acid and 7-β-D-mandelamido-7α-methoxy-3-[1-(2-carbamoylethyl)tetrazol-5-ylthiomethyl]-3-cephem-4-carboxylic acid.

The compounds of Formula IV are, preferably, prepared by acylation of a 7β-amino-7α-methoxy-3-substituted tetrazolylthiomethyl cephalosporin nucleus of Formula V:

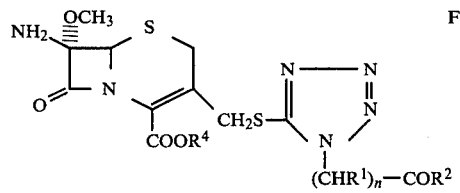

FORMULA V in which $R^1$, $R^2$, $R^4$ and n are as previously defined hereabove with an appropriate acylating agent, suitably protected as necessary, by the procedures described above followed by removal of the protective groups when present also as described above. The compounds of Formula V are also considered objects of this invention.

The 7β-amino-7α-methoxy cephalosporin nuclei of Formula V are prepared by reaction of a 7-amino cephalosporin of Formula II where $R^4$ is a protecting ester group such as a t-butyl group and, when $R^2$ is hydroxy, this acid group is also protected for example as a t-butyl ester, with 3,5-di-t-butyl-4-hydroxybenzaldehyde with azeotropic removal of water. Subsequent treatment of the product thus formed with lead dioxide and reaction of the oxidized intermediate with methanol followed by cleavage of the imine function with, for example, Girard reagent T (trimethylaminoacetohydrazide chloride), followed by removal of the protective group(s) as desired gives the compounds of Formula V.

As with the compounds of Formula I, all non-toxic pharmaceutically acceptable salts and all isomers, including separated isomers and mixtures thereof, of the compounds represented by Formula IV are included within the scope of this invention.

The compounds of Formula IV have anti-bacterial activity against both gram-positive and gram-negative organisms. They are administered and formulated in the same manner as previously described for the compounds of Formula I.

The following examples illustrate the invention, but are not to be construed as limiting the scope thereof. Temperatures are in degrees Centigrade unless otherwise stated.

EXAMPLE 1

7-D-Mandelamido-3-(1-carboxymethyltetrazol-5-ylthiomethyl)-3-cephem-4-carboxylic acid (I)

Glycine (60 g., 0.8 mol.) was added to a cooled (5°–10°) solution of 89.6 g. (1.6 mol.) of potassium hydroxide in 200 ml. of water. After complete dissolution 60.8 g. (0.8 mol.) of carbon disulfide was added and the reaction mixture was stirred at 25° for three hours. A solution of 113.6 g. (0.8 mol.) of methyl iodide in 200 ml. of ethanol was added while maintaining the temperature at 25°–30°. The reaction mixture was stirred for two hours at 25°, then concentrated in vacuo and the remaining aqueous phase was basicified to pH 8.0 with aqueous sodium carbonate and extracted with ether. The aqueous phase was acidified to pH 2.5 with dilute hydrochloric acid and extracted with ethyl acetate. The extract was concentrated in vacuo and the residue recrystallized from toluene to give methyl carboxymethyldithiocarbamate.

A mixture of 16.5 g. (0.1 mol.) of methyl carboxymethyldithiocarbamate and 14.3 g. (0.22 mol.) of sodium azide in 150 ml. of water was heated at 56° for 12 hours. The reaction mixture was extracted with ether, then acidified to pH 1.5 with dilute hydrochloric acid and extracted with ethyl acetate. The extract was dried (MgSO$_4$) and evaporated to dryness to give 1-carboxymethyl-tetrazole-5-thiol, m.p. 178°–179°.

1-Carboxymethyltetrazole-5-thiol was also prepared by refluxing a mixture of 45.95 g. (0.316 mol.) of ethyl isothiocyanoacetate and 30.8 g. (0.475 mol.) of sodium azide in 500 ml. of water for 2.75 hours. Ethyl acetate (400 ml.) was added to the cooled reaction mixture and it was acidified to pH 1.9 with 3 N hydrochloric acid. The layers were separated, the aqueous phase was extracted three times with ethyl acetate and the combined extracts were dried (MgSO$_4$) and evaporated to dryness to give a residue which was chromatographed on silica gel with 17:3:2 chloroform-isopropanol-formic acid to give the tetrazole thiol.

A mixture of 4.49 g. (10 mmol.) of 7-D-mandelamidocephalosporanic acid sodium salt, 2.40 g. (15 mmol.) of 1-carboxymethyltetrazole-5-thiol and 2.52 g. (30 mmol.) of sodium bicarbonate in 40 ml. of water was heated at 70° for four hours. The reaction mixture was cooled (ice bath) and acidified to pH 1.8 with 3 N hydrochloric acid. Ethyl acetate was added, the layers were separated and the organic phase was dried (MgSO$_4$). Ether was added to the ethyl acetate solution, the solution was filtered, ether and petroleum ether were added to the filtrate and the resulting precipitate was collected, decolorized in ethyl acetate solution and re-precipitated by addition of ether and petroleum ether to give the title compound.

The title compound was dissolved in methanol and the methanol solution was treated with 26 ml. of 0.196 N sodium methoxide in methanol. The methanol was removed in vacuo and the residue was dissolved in a minimum amount of water to which isopropanol was added to give 7-D-mandelamido-3-(1-carboxymethyltetrazol-5-ylthiomethyl)-3-cephem-4-carboxylic acid sodium salt.

$C_{19}H_{17}N_6O_7S_2Na \cdot 2 H_2O \cdot C_3H_8O$—
Calculated: 42.30% C; 4.67% H; 13.45% N.
Found: 42.67% C; 4.56% H; 13.39% N.

EXAMPLE 2

7-(D-α-Amino-4-hydroxyphenylacetamido)-3-(1-carboxymethyl-tetrazol-5-ylthiomethyl)-3-cephem-4-carboxylic acid (II)

A solution of 5.22 g. (10.0 mmol.) of 7-(D-α-t-butoxycarbonylamino-4-hydroxyphenylacetamido)cephalosporanic acid and 2.40 g. (15.0 mmol.) of 1-carboxymethyltetrazole-5-thiol in 75 ml. of pH 6.4 phosphate buffer solution was treated with sufficient solid sodium bicarbonate to give a pH of 6.4. The mixture was heated at 70° for 4.5 hours, cooled and chromatographed on silica gel with 15:5:2 chloroform-isopropanol-formic acid as eluant to give 7-(D-α-t-butoxycarbonylamino-4-hydroxyphenylacetamido)-3-(1-carboxymethyltetrazol-5-ylthiomethyl)-3-cephem -4-carboxylic acid.

7-(D-α-t-butoxycarbonylamino-4-hydroxyphenylacetamido)-3-(1-carboxymethyltetrazol-5-ylthiomethyl)-3-cephem-4-carboxylic acid was stirred at 25° with 25 ml. of trifluoroacetic acid and 25 ml. of 1,3-dimethoxybenzene for 1.25 hours. The mixture was evaporated to dryness, ether was added to the residue and the precipitated salt was collected and dissolved in 350 ml. of water containing a few drops of trifluoroacetic acid. The aqueous solution was treated with excess Amberlite IR-45 ion-exchange resin to pH 2.7, then lyophilized to give the title compound.

$C_{19}H_{19}N_7O_7S_2 \cdot 2 H_2O$—
Calculated: 41.70% C; 4.36% H; 17.22% N.
Found: 42.05% C; 4.08% H; 16.30% N.

EXAMPLE 3

7-D-Mandelamido-3-(1-N-methylcarbamoylmethyltetrazol-5-ylthiomethyl)-3-cephem-4-carboxylic acid (III)

A solution of 7.2 g. (44 mmol.) of 1,1-carbonyldiimidazole in 110 ml. of dry tetrahydrofuran and 20 ml. of dimethylformamide was added to a solution of 7.0 g. (43.8 mmol.) of 1-carboxymethyltetrazole-5-thiol in 110 ml. of dry tetrahydrofuran and 20 ml. of dimethylformamide. Tetrahydrofuran saturated with methyl amine was added and the reaction mixture was stirred at 25° for 12 hours. The mixture was concentrated, the residue was diluted with 200 ml. of water and the resulting solution was adjusted to pH 2–3 by addition of 3 N hydrochloric acid. The aqueous solution was extracted with ethyl acetate and the extract was dried (MgSO$_4$) was evaporated to dryness. Ethyl acetate (15 ml.) and ether (10 ml.) were added to the residue and it was cooled to induce crystallization of 1-N-methyl-carbamoylmethyltetrazole-5-thiol, m.p. 137°–140°.

1-N-Methylcarbamoylmethyltetrazole-5-thiol (2.39 g., 10 mmol.) and 4.22 g. (9.4 mmol.) of 7-D-mandelamidocephalosporanic acid sodium salt were reacted as described in the procedure of Example 1. After cooling, the reaction mixture was acidified to pH 4 with 3 N hydrochloric acid, refrigerated for 12 hours and extracted with ethyl acetate. The extract was dried (Na$_2$SO$_4$) and evaporated to dryness to give a residue which was dissolved in 5 ml. of absolute methanol and 15 ml. of ethyl acetate. To this solution was added 1 ml. of ethyl acetate containing 0.1 ml. of cyclohexylamine and 100 ml. of ethyl acetate. The precipitate was collected and dissolved in absolute methanol and the solution was added to 300 ml. of ethyl acetate. The resulting precipitate was collected and dissolved in 70 ml. of water and 70 ml. of chloroform at pH 2. The layers were separated, the aqueous phase was extracted with ethyl acetate and the combined extracts were dried ($Na_2SO_4$) and recrystallized from ethyl acetate-ether to give the title compound.

$C_{20}H_{20}N_7O_6S_2 \cdot 0.7\ C_4H_8O_2 \cdot 0.5\ H_2O$—
Calculated: 46.39% C; 4.71% H; 16.61% N.
Found: 46.78% C; 4.35% H; 16.36% N.

EXAMPLE 4

7-D-Mandelamido-3-(1-N,N-dimethylcarbamoylmethyltetrazol-5-ylthiomethyl)-3-cephem-4-carboxylic acid (IV)

To a solution of 5.42 g. (33.8 mmol.) of 1-carboxymethyltetrazole-5-thiol in 75 ml. of dry tetrahydrofuran and 20 ml. of dry dimethylformamide was slowly added a solution of 5.49 g. (33.9 mmol.) of 1,1-carbonyldiimidazole in 95 ml. of dry dimethylformamide. The reaction mixture was stirred for 35 minutes, then 250 ml. of tetrahydrofuran saturated with dimethylamine was added to the suspension and it was stirred at 25° for 12 hours. The mixture was concentrated to about 200 ml. and tetrahydrofuran and ether were added. The precipitate was collected by filtration and dissolved in 170 ml. of water. The aqueous solution was acidified to pH 2.0 by addition of 6 N sulfuric acid and extracted with ethyl acetate. The ethyl acetate solution was evaporated to dryness and the residue was triturated with ether containing 5% ethyl acetate to give 1-N,N-dimethylcarbamoylmethyltetrazole-5-thiol, m.p. 190°–200° (dec.).

7-D-Mandelamidocephalosporanic acid sodium salt hydrate (3.59 g., 8 mmol.) was added to a solution of 1.008 g. (12 mmol.) of sodium bicarbonate and 2.244 g. (12 mmol.) of 1-N,N-dimethylcarbamoylmethyltetrazole-5-thiol in 40 ml. of water and the reaction mixture was heated at 67° for four hours. After cooling, the mixture was acidified to pH 5.0 with 3 N hydrochloric acid and repeatedly extracted with ethyl acetate. The combined extracts were dried ($MgSO_4$) and evaporated to dryness to give the title compound.

The title compound was dissolved in methanol and the solution was added to a mixture of 100 ml. of chloroform and 300 ml. of ether. The resulting precipitate was collected and recrystallized from methanol containing cyclohexylamine to give the title compound as its cyclohexylamine salt.

$C_{21}H_{23}N_7O_6S_2 \cdot 1.5\ H_2O \cdot C_6H_{13}N$—
Calculated: 49.15% C; 5.95% H; 16.98% N.
Found: 49.49% C; 5.38% H; 16.42% N.

EXAMPLE 5

7-D-Mandelamido-3-(1-carbamoylmethyltetrazol-5-ylthiomethyl)-3-cephem-4-carboxylic acid (V)

1-Carboxymethyltetrazole-5-thiol and 1,1-carbonyldiimidazole were reacted as described in Example 4. To the reaction mixture was added tetrahydrofuran saturated with dry ammonia gas. The resulting suspension was stirred for 2.5 hours and the solid which formed was collected by filtration, washed with tetrahydrofuran and dissolved in methanol. Amberlite IR-120 ion-exchange resin (50 g.) was added and the suspension was stirred for 15 minutes. The resin was then removed and washed with absolute methanol. The methanol solution was concentrated to give 1-carbamoylmethyltetrazole-5-thiol, m.p. 200° (dec.).

1-Carbamoylmethyltetrazole-5-thiol (0.715 g., 4.5 mmol.) and 1.347 g. (3.0 mmol.) of 7-D-mandelamidocephalosporanic acid sodium salt were reacted as described in the procedure of Example 1. After cooling, the reaction mixture was acidified to pH 2.0 and extracted with ethyl acetate until no product remained in the aqueous phase. The extracts were combined, dried ($MgSO_4$) and the solvent evaporated to give a residue which was dissolved in 20 ml. of acetone and 10 ml. of benzene. Cyclohexylamine (1.2 mmol.) was added to the solution and the precipitated salt was collected, washed with acetone-benzene (2:1) and dissolved in 40 ml. of water. The pH of the aqueous solution was adjusted to 3 and the solution was extracted with ethyl acetate. The extracts were dried ($MgSO_4$) and evaporated to dryness to give the title compound.

$C_{19}H_{19}N_7O_6S_2\ hu\ \cdot 0.5 \cdot H_2O \cdot 1\ C_4H_8O_2$—
Calculated: 45.84% C; 4.68% H; 16.26% N.
Found: 45.52% C; 4.34% H; 15.90% N.

EXAMPLE 6

7-(D-α-Amino-4-hydroxyphenylacetamido)-3-(1-carbamoylmethyltetrazol-5-ylthiomethyl)-3-cephem-4-carboxylic acid (VI)

A solution of 5.21 g. (0.01 mol.) of 7-(D-α-t-butoxycarbonylamino-4-hydroxyphenylacetamido)cephalosporanic acid and 2.4 g. (0.015 mol.) of 1-carbamoylmethyltetrazole-5-thiol were reacted according to the procedure described in Example 2. After cooling, the reaction mixture was extracted with ethyl acetate. Fresh ethyl acetate was added to the aqueous phase and it was acidified with stirring to pH 2.8 with 6 N sulfuric acid. The layers were separated and the aqueous phase was again extracted with ethyl acetate. The combined extracts were washed with water, dried ($MgSO_4$) and the solvent evaporated to give a solid which was recrystalized from acetone-chloroform and chromatographed on silica to give 7-(D-α-t-butoxycarbonyl-amino-4-hydroxyphenylacetamido)-3-(1-carbamoylmethyltetrazol-5-ylthiomethyl)-3-cephem-4-carboxylic acid.

7-(D-α-t-Butoxycarbonylamino-4-hydroxyphenylacetamido)-3-(1-carbamoylmethyltetrazol-5-ylthiomethyl)-3-cephem-4-carboxylic acid was treated with trifluoroacetic acid as described in Example 2 to give the title compound.

$C_{19}H_{20}N_8O_6S_2 \cdot 3.5\ H_2O$—Calculated: 39.10% C; 4.66% H; 19.20% N. Found: 41.64% C; 4.39% H; 20.06% N.

EXAMPLE 7

7-D-Mandelamido-3-[1-(2-carboxyethyl)tetrazol-5-ylthiomethyl]-3-cephem-4-carboxylic acid (VIII)

β-Alanine (17.8 g., 0.2 mol.) was added to a solution of 22.4 g. (0.4 mol.) of potassium hydroxide in 500 ml. of water at 25°. Carbon disulfide (12.2 ml., 0.2 mol.) was added and the reaction mixture was refluxed for three hours. The mixture was cooled, 28.4 g. (0.2 mol.) of methyl iodide and 500 ml. of ethanol were added and the resulting mixture was stirred for 30 minutes. The precipitate was collected by filtration, the filtrate was concentrated and the aqueous residue was combined with the solid material and brought to pH 8.5–9 by addition of 10% aqueous sodium hydroxide. The resulting suspension was extracted with ethyl acetate. Ethyl acetate was added to the aqueous phase which was then acidified to pH 1.5 with 6N hydrochloric acid. The layers were separated and the aqueous phase was extracted with ethyl acetate. The ethyl acetate extracts were combined, dried (MgSO$_4$) and evaporated to dryness to give methyl 2-carboxyethyldithiocarbamate.

To a mixture of 25.37 g. (0.143 mol.) of methyl 2-carboxyethyldithiocarbamate and 5.6 g. (0.143 mol.) of sodium hydroxide in 210 ml. of water was added 9.25 g. (0.143 mol.) of sodium azide. The reaction mixture was refluxed for one hour then cooled, diluted with 100 ml. of ether and acidified to pH 1.7. The layers were separated, the aqueous phase was extracted with ether and the combined extracts were dried (MgSO$_4$) and evaporated to dryness to give a residue which was recrystallized from acetone-chloroform to give 1-(2-carboxyethyl)tetrazole-5-thiol, m.p. 158°–160°.

Substitution of an equivalent amount of 1-(2-carboxyethyl)tetrazole-5-thiol in the procedure of Example 1 in place of 1-carboxymethyltetrazole-5-thiol gave the title compound.

$C_{20}H_{20}N_6O_7S_2.0.5$ $H_2O.0.1$ $C_4H_{10}O$—Calculated: 45.63% C; 4.13% H; 15.65% N. Found: 45.82% C; 4.14% H; 14.22% N.

EXAMPLE 8

7-D-Mandelamido-3-[1-(2-carbamoylethyl)tetrazol-5-ylthiomethyl]-3-cephem-4-carboxylic acid (VII)

When an equivalent amount of 1-(2-carboxyethyl)tetrazole-5-thiol was substituted in the procedure of Example 5 for 1-carboxymethyltetrazole-5-thiol, 1-(2-carbamoylethyl)tetrazole-5-thiol was obtained, m.p. 181°–182° (dec.).

1-(2-Carbamoylethyl)tetrazole-5-thiol (1.73 g., 0.01 mol.) and 3.02 g. (6.7 mmol.) of 7-D-mandelamido-cephalosporanic acid were reacted according to the procedure of Example 2 while maintaining the pH at 7.0 by addition of sodium bicarbonate. The cooled solution was acidified to pH 5.0 with 6N sulfuric acid and then extracted with ethyl acetate. The aqueous phase was acidified to pH 2.1 and extracted with ethyl acetate. The extract was washed with water, dried (MgSO$_4$) and evaporated to dryness to give a residue which was chromatographed on silica to give the title compound as a glassy solid which crystallized from methanol-ether.

$C_{20}H_{21}N_7O_6S_2.1.25$ $H_2O.0.2$ $C_4H_{10}O$—Calculated: 44.85% C; 4.61% H; 17.60% N. Found: 45.30% C; 4.31% H; 16.98% N.

EXAMPLE 9

7-(D-α-Amino-4-hydroxyphenylacetamido)-3-(1-N,N-dimethylcarbamoylmethyltetrazol-5-ylthiomethyl)-3-cephem-4-carboxylic acid (IX)

A solution of 4.26 g. (8.18 mmol.) of 7-(D-α-t-butoxycarbonylamino-4-hydroxyphenylacetamido)cephalosporanic acid and 2.3 g. (0.012 mol.) of 1-N,N-dimethylcarbamoylmethyltetrazole-5-thiol were reacted according to the procedure described in Example 2. After cooling, the reaction mixture was extracted with ethyl acetate. Fresh ethyl acetate was added to the aqueous phase and it was acidified to pH 2.5 with 6N sulfuric acid. The layers were separated and the aqueous phase was again extracted with ethyl acetate. The combined extracts were washed with water, dried (Na$_2$SO$_4$) and evaporated to dryness to give a residue which was chromatographed on silica to give 7-(D-α-t-butoxycarbonylamino-4-hydroxyphenylacetamido)-3-(1-N,N-dimethylcarbamoylmethyltetrazol-5-ylthiomethyl)-3-cephem-4-carboxylic acid.

7-(D-α-t-Butoxycarbonylamino-4-hydroxyphenylacetamido)-3-(1-N,N-dimethylcarbamoylmethyltetrazol-5-ylthiomethyl)-3-cephem-4-carboxylic acid was treated with trifluoroacetic acid as described in Example 2 to give the title compound.

$C_{21}H_{24}N_8O_6S_2.2.5$ $H_2O$—Calculated: 42.86% C; 4.94% H; 18.85% N. Found: 43.05% C; 4.81% H; 17.65% N.

EXAMPLE 10

7-(D-α-Amino-4-hydroxyphenylacetamido)-3-[1-(2-carbamoylethyl)tetrazol-5-ylthiomethyl]-3-cephem-4-carboxylic acid (X)

A mixture of 3.9 g. (0.022 mol.) of 1-(2-carbamoylethyl)tetrazole-5-thiol and 7.82 g. (0.015 mol.) of 7-(D-α-t-butoxycarbonylamino-4-hydroxyphenylacetamido)-cephalosporanic acid was reacted by the procedure described in Example 2 with addition of sodium bicarbonate to give a pH of 6.8. After cooling, the reaction mixture was extracted with ethyl acetate. Fresh ethyl acetate was added to the aqueous phase and it was acidified to pH 1.8. The layers were separated and the aqueous phase was again extracted with ethyl acetate. The extract was dried (MgSO$_4$) and evaporated to dryness to give a residue which was chromatographed on silica gel with 7.5:2.4:1 chloroform-ethanol-formic acid as eluant to give 7-(D-α-t-butoxycarbonylamino-4-hydroxyphenylacetamido)-3-[1-(2-carbamoylethyl)tetrazol-5-ylthiomethyl]-3-cephem-4-carboxylic acid.

7-(D-α-t-Butoxycarbonylamino-4-hydroxyphenylacetamido)-3-[1-(2-carbamoylethyl)tetrazol-5-ylthiomethyl]-3-cephem-4-carboxylic acid was treated with trifluoroacetic acid as described in the procedure of Example 2 to give the title compound.

$C_{20}H_{22}N_8O_6S_2.1.5$ $H_2O$—Calculated: 42.77% C; 4.49% H; 19.95% N. Found: 42.70% C; 4.47% H; 19.06% N.

EXAMPLE 11

7-D-Mandelamido-3-[1-(3-carboxypropyl)tetrazol-5-ylthiomethyl]-3-cephem-4-carboxylic acid (XII)

When an equivalent amount of 4-aminobutyric acid was substituted in the procedure of Example 7 for β-alanine, methyl 3-carboxypropyldithiocarbamate was prepared.

Reaction of methyl 3-carboxypropyldithiocarbamate with sodium azide and sodium hydroxide as described in Example 7 gave 1-(3-carboxypropyl)tetrazole-5-thiol, m.p. 99°–101°.

Substitution of an equivalent amount of 1-(3-carboxypropyl)tetrazole-5-thiol in the procedure of Example 1 in place of 1-carboxymethyltetrazole-5-thiol gave the title compound.

The title compound was converted to the corresponding sodium salt as described in the procedure of Example 1.

$C_{21}H_{21}N_6O_7S_2.Na.0.75$ $H_2O$—Calculated: 44.25% C; 3.97% H; 14.74% N. Found: 43.99% C; 3.91% H; 14.71% N.

EXAMPLE 12

7-D-Mandelamido-3-[1-(3-carbamoylpropyl)tetrazol-5-ylthiomethyl]-3-cephem-4-carboxylic acid (XI)

When an equivalent amount of 1-(3-carboxypropyl)-tetrazole-5-thiol was substituted in the procedure of Example 5 for 1-carboxymethyltetrazole-5-thiol, 1-(3-carboxypropyl)tetrazole-5-thiol was obtained, m.p. 133°–136°.

1-(3-Carbamoylpropyl)tetrazole-5-thiol (3.34 g., 18 mmol.) and 5.39 g. (12 mmol.) of 7-D-mandelamidocephalosporanic acid were reacted according to the procedure of Example 2 while maintaining the pH at 6.6 by addition of sodium bicarbonate. The cooled reaction mixture was acidified to pH 2.5 and extracted with ethyl acetate. The extract was evaporated to dryness, the residue was precipitated from ethyl acetate-ether and the precipitate was chromatographed on silica gel with 8:2:1 chloroform-ethanol-formic acid to give the title compound.

$C_{21}H_{23}N_7O_6S_2.2$ $H_2O$—Calculated: 44.27% C; 4.77% H; 17.21% N. Found: 44.46% C; 4.37% H; 16.87% N.

EXAMPLE 13

7-D-Mandelamido-3-[1-(5-carboxypentyl)tetrazol-5-ylthiomethyl]-3-cephem-4-carboxylic acid (XIII)

Substitution of an equivalent amount of 6-aminocaproic acid in the procedure of Example 7 for β-alanine gave methyl 5-carboxypentyldithiocarbamate.

Reaction of methyl 5-carboxypentyldithiocarbamate with sodium azide and sodium hyroxide as described in Example 7 gave 1-(5-carboxypentyl)tetrazole-5-thiol, m.p. 100°–100.5°.

Substitutions of an equivalent amount of 1-(5-carboxypentyl)-tetrazole-5-thiol in the procedure of Example 1 in place of 1-carboxymethyltetrazole-5-thiol gave the title compound.

The title compound was converted to the corresponding sodium salt by treatment with sodium methoxide as described in Example 1.

$C_{23}H_{25}N_6O_7S_2.Na.0.75$ $H_2O$—Calculated: 46.19% C; 4.47% H; 14.05% N. Found: 46.07% C; 4.48% H; 13.76% N.

EXAMPLE 14

7-D-Mandelamido-3-[1-(5-carbamoylpentyl)tetrazol-5-ylthiomethyl]-3-cephem-4-carboxylic acid (XIV)

1-(5-Carboxypentyl)tetrazole-5-thiol (6.0 g., 28 mmol.) was slowly dissolved in 20 ml. of thionyl chloride and the mixture was stirred at 25° for 1.5 hours. Evaporation of the reaction mixture to dryness gave a residue which was dissolved in 30 ml. of tetrahydrofuran. The tetrahydrofuran solution was added to a cold mixture of 60 ml. of ammonium hydroxide and 30 ml. of tetrahydrofuran and the resulting mixture was stirred at 25° for two days. The mixture was extracted with ethyl acetate. The aqueous phase was acidified to pH 1 by addition of 6N hydrochloric acid to precipitate 1-(5-carbamoylpentyl)tetrazole-5-thiol, m.p. 155°–157°.

1-(5-Carbamoylpentyl)tetrazole-5-thiol (1.6 g., 7.5 mmol.) and 1.79 g. (4 mmol.) of 7-D-mandelamidocephalosporanic acid were reacted according to the procedure of Example 2 while maintaining the pH at 6.8 by addition of sodium bicarbonate. The cooled reaction mixture was acidified to pH 2.5 and extracted with ethyl acetate. The extract was evaporated to dryness and the residue was chromatographed on silica gel with 7:3:1 chloroform-ethanol-formic acid as eluant to give the title compound.

The title compound was converted to the corresponding sodium salt as described in Example 1 above.

$C_{23}H_{26}N_7O_6S_2.Na.1.5$ $H_2O$—Calculated: 45.24% C; 4.78% H; 16.01% N. Found: 45.31% C; 4.50% H; 15.62% N.

EXAMPLE 15

7-Trifluoromethylmercaptoacetamido-3-[1-(2-carboxyethyl)tetrazol-5-ylthiomethyl]-3-cephem-4-carboxylic acid (XV)

To an aqueous solution of 2.12 g. (12.2 mmol.) of 1-(2-carboxyethyl)tetrazole-5-thiol and 2.05 g. (24.4 mmol.) of sodium bicarbonate in 35 ml. of water was added 3.66 g. (8.1 mmol.) of 7-trifluoromethylmercaptoacetamidocephalosporanic acid. The reaction mixture was stirred at 70° for 4.5 hours, then cooled and chromatographed on XAD-2 resin with water and methanol as eluants. The methanol solution was evaporated to dryness to give a residue which was stirred with 30 ml. of water. Ethyl acetate was added and the resulting mixture was filtered and lyophilized to give 7-tri fluoromethylmercaptoacetamido-3-[1-(2-carboxyethyl)tetrazol-5-ylthiomethyl]-3-cephem-4-carboxylic acid disodium salt.

$C_{15}H_{13}F_3N_6O_6S_3.2$ $Na.1.5H_2O$—Calculated: 30.26% C; 2.75% H; 13.93% N. Found: 30.62% C; 2.73% H; 13.41% N.

7-Trifluoromethylmercaptoacetamido-3-[1-(2-carboxyethyl)tetrazol-5-ylthiomethyl]-3-cephem-4-carboxylic acid disodium salt is dissolved in a minimum amount of water to which chloroform is added. While stirring, 3N hydrochloric acid is added until the solution is acidified to pH 2.5. The layers are separated, the aqueous phase is extracted with chloroform and the combined extracts are washed with water, dried (MgSO$_4$) and evaporated to dryness to give the title compound.

EXAMPLE 16

7-Trifluoromethylmercaptoacetamido-3-(1-carbamoylmethyltetrazol-5-ylthiomethyl)-3-cephem-4-carboxylic acid (XVII)

7-Trifluoromethylmercaptoacetamido-3-(1-carbamoylmethyltetrazol-5-ylthiomethyl)-3-cephem-4-carboxylic acid sodium salt was prepared by reaction of 2.39 g. (15 mmol.) of 1-carbamoylmethyltetrazole-5-thiol, 1.27 g. (15 mmol.) of sodium bicarbonate and 4.52 g. (10 mmol.) of 7-trifluoromethylmercaptoacetamidocephalosporanic acid by the procedure described in Example 15.

$C_{14}H_{13}F_3N_7O_5S_3.Na.1.5$ $H_2O$ · $0.1C_4H_{10}O$—Calculated: 30.34% C; 3.00% H; 17.02% N. Found: 30.76% C; 2.45% H; 18.31% N.

The title compound is obtained from the salt as described in Example 15.

EXAMPLE 17

7-Amino-3-[1-(2-carbamoylethyl)tetrazol-5-ylthiomethyl]-3-cephem-4-carboxylic acid A solution of 1-(2-carbamoylethyl)tetrazole-5-thiol (10.4 g., 0.06 mol.) in 120 ml. of acetone was added to a warm (45°) solution of 10.9 g. (0.04 mol.) of 7-aminocephalosporanic acid in a mixture of 220 ml. of water, 50 ml. of acetone and 8.4 g. (0.01 mol.) of sodium bicarbonate. The temperature was raised to 65° and the pH maintained at 7.4–7.6 by addition of aqueous sodium carbonate solution. After three hours, the reaction mixture was cooled to 10° and adjusted to pH 3.5 by addition of dilute hydrochloric acid. The resulting solid was collected by filtration, washed with water and acetone and suspended in 95 ml. of 1.5N hydrochloric acid. The acid suspension was stirred at 25° for five hours, filtered and the pH of the filtrate was adjusted to 3.5 by addition of solid sodium bicarbonate. The solid was collected by filtration and washed with water and acetone to give the title compound.

EXAMPLE 18

7-Trifluoromethylmercaptoacetamido-3-[1-(2-carbamoylethyl)tetrazol-5-ylthiomethyl]-3-cephem-4-carboxylic acid (XVI)

A solution of 4.8 g. (0.03 mol.) of trifluoromethylmercaptoacetic acid and 3.45 g. (0.03 mol.) of N-hydroxysuccinimide in 50 ml. of tetrahydrofuran was stirred and cooled to 0° before 6.2 g. (0.031 mol.) of dicyclohexylcarbodiimide was added in one portion. The reaction mixture was stirred at 0° for one hour and then for 12 hours at 25°. The precipitate was collected by filtration and washed with tetrahydrofuran. The solid was dissolved in ether and the solution was decolorized with charcoal and filtered. The filtrate was evaporated to give the activated ester of trifluoromethylmercaptoacetic acid.

A suspension of 3.85 g. (0.01 mol.) of 7-amino-3-[1-(2-carbamoylethyl)tetrazol-5-ylthiomethyl]-3-cephem-4-carboxylic acid in 50 ml. of dry dimethylformamide was treated with 2 ml. of triethylamine and the mixture was stirred for 15 minutes at 25°. The activated ester of trifluoromethylmercaptoacetic acid (2.57 g., 0.016 mol.) was added to the mixture and it was stirred an additional hour. The reaction mixture was evaporated to dryness and water and ethyl acetate were added to the residue. The layers were separated, ethyl acetate was added to the aqueous phase and it was acidified to pH 2.5 by addition of 6N hydrochloric acid. The mixture was filtered, the layers were separated and the aqueous phase was extracted with ethyl acetate. The extract was washed with water, dried (MgSO$_4$) and evaporated to dryness to give the title compound.

The title compound was dissolved in 30 ml. of methanol and a 5% solution of sodium methoxide in methanol was added until pH 6.9. Ether was added and the resulting precipitate was collected and washed with ether to give 7-trifluoromethylmercaptoacetamido-3-[1-(2-carbamoylethyl)tetrazol-5-ylthiomethyl]-3-cephem-4-carboxylic acid sodium salt.

$C_{15}H_{15}F_3N_7O_5S_3$.Na—Calculated: 32.79% C; 2.75% H; 17.84% N. Found: 32.52% C; 2.79% H; 17.54% N.

EXAMPLE 19

7-D-Mandelamido-3-[1-(10-carboxydecyl)tetrazol-5-ylthiomethyl]-3-cephem-4-carboxylic acid A suspension of 56 g. (1.0 mol.) of potassium hydroxide and 100 g. (0.5 mol.) of 11-aminoundecanoic acid in 170 ml. of water was stirred for 30 minutes at 25° then 40 g. (0.52 mol.) of carbon disulfide and 80 ml. of ethanol were added and the reaction mixture was stirred at 25° for 12 hours. The mixture was refluxed gently for two hours and cooled. Methyl iodide (71 g., 0.3 mol.) and 130 ml. of ethanol were added to the mixture and it was stirred at 25° for 12 hours. The mixture was evaporated to remove the ethanol and the solid residue was collected by filtration to give methyl 10-carboxydecyldithiocarbamate.

Methyl 10-carboxydecyldithiocarbamate (28 g., 0.096 mol.) was reacted with 6.5 g. (0.1 mol.) of sodium azide according to the procedure described in Example 7. Acidification upon work-up gave 1-(10-carboxydecyl)tetrazole-5-thiol as a white precipitate, m.p. 95°–98°.

1-(10-Carboxydecyl)tetrazole-5-thiol (4.29 g., 15 mmol.) was slowly added to a solution of 3.36 g. (40 mmol.) of sodium bicarbonate in 100 ml. of water. Ethanol (30 ml.) was then added followed by 4.20 g. (10 mmol.) of 7-D-mandelamidocephalosporanic acid and the mixture was heated at 65° for 3.5 hours. Upon cooling, a precipitate formed which was collected by filtration. The filtrate was extracted with ethyl acetate, the aqueous layer was acidified to pH 4 and extracted again with ethyl acetate. The extract was dried (MgSO$_4$) and evaporated to dryness to give the title compound.

The title compound was converted to the corresponding sodium salt as described above.

$C_{28}H_{35}N_6O_7S_2$. Na—
Calculated: 48.01% C; 5.71% H; 12.00% N.
Found: 48.42% C; 5.13% H; 11.35% N.

EXAMPLE 20

7-D-Mandelamido-3-[1-(10-carbamoyldecyl)tetrazol-5-ylthiomethyl]-3-cephem-4-carboxylic acid 1-(10-Carbamoyldecyl)tetrazole-5-thiol was prepared from 1-(10-carboxydecyl)tetrazole-5-thiol by the procedure described in Example 5, m.p. 112°–114°.

Reaction of 1-(10-carbamoyldecyl)tetrazole-5-thiol and 7-D-mandelamidocephalosporanic acid as described in Example 19 gave the title compound.

EXAMPLE 21

7-D-Mandelamido-3-[1-(2-carboxy-1-methylethyl)tetrazol-5-ylthiomethyl]-3-cephem-4-carboxylic acid Substitution of an equivalent amount of 3-aminobutyric acid in the procedure of Example 7 for β-alanine gave methyl (2-carboxy-1-methyl)ethyldithiocarbamate.

Treatment of methyl (2-carboxy-1-methyl)ethyldithiocarbamate with sodium azide also as described in Examplea 7 gave 1-(2-carboxy-1-methylethyl)tetrazole-5-thiol, m.p. 169°–172°.

7-D-Mandelamidocephalosporanic acid and 1-(2-carboxy-1-methylethyl)tetrazole-5-thiol were reacted in the presence of excess sodium bicarbonate as described in Example 2 to give the title compound.

The title compound was converted to the corresponding sodium salt as previously described.

$C_{21}H_{21}N_6O_7S_2$. Na . $2H_2O$—
Calculated: 42.56% C; 4.22% H; 14.18% N.
Found: 42.83% C; 3.88% H; 13.26% N.

EXAMPLE 22

When an equivalent amount of an amino acid listed below:
alanine
2-aminobutyric acid
2-aminovaleric acid
2-aminohexanoic acid
is used in the procedure of Example 7 in place of β-alanine and the resulting dithiocarbamates are treated with sodium azide as described therein, the following substituted tetrazole thiols are obtained:

1-(1-carboxyethyl)tetrazole-5-thiol
1-(1-carboxypropyl)tetrazole-5-thiol
1-(1-carboxybutyl)tetrazole-5-thiol
1-(1-carboxypentyl)tetrazole-5-thiol.

Reaction of a tetrazole thiol listed above with 7-D-mandelamidocephalosporanic acid as described hereinabove gives the following compounds of this invention:

7-D-mandelamido-3-[1-(1-carboxyethyl)tetrazol-5-ylthiomethyl]-3-cephem-4-carboxylic acid
7-D-mandelamido-3-[1-(1-carboxypropyl)tetrazol-5-ylthiomethyl]-3-cephem-4-carboxylic acid
7-D-mandelamido-3-[1-(1-carboxybutyl)tetrazol-5-ylthiomethyl]-3-cephem-4-carboxylic acid
7-D-mandelamido-3-[1-(1-carboxypentyl)tetrazol-5-ylthiomethyl]-3-cephem-4-carboxylic acid.

Likewise, reaction of a substituted tetrazole thiol listed above with 7-aminocephalosporanic acid, 7-(D-α-t-butoxycarbonyl-4-hydroxyphenylacetamido)cephalosporanic acid or 7-trifluoromethylmercaptoacetamidocephalosporanic acid according to the procedures described herein with subsequent removal of the protective groups as necessary, gives the corresponding 7-amino-3-(carboxyalkyltetrazol-5-ylthiomethyl)-3-cephem-4-carboxylic acids, 7-(D-α-amino-4-hydroxyphenylacetamido)-3-(carboxyalkyltetrazol-5-ylthiomethyl)-3-cephem-4-carboxylic acids and 7-trifluoromethylmercaptoacetamido-3-(carboxyalkyltetrazol-5-ylthiomethyl)-3-cephem-4-carboxylic acids.

EXAMPLE 23

Reaction of an acid substituted tetrazole thiol listed in Examples 21 or 22 with 1,1-carbonyldiimidazole and ammonia as described in the procedure of Example 5 gives the following carbamoylalkyl substituted tetrazole thiols:

1-(2-carbamoyl-1-methylethyl)tetrazole-5-thiol
1-(1-carbamoylethyl)tetrazole-5-thiol
1-(1-carbamoylpropyl)tetrazole-5-thiol
1-(1-carbamoylbutyl)tetrazole-1-thiol
1-(1-carbamoylpentyl)tetrazole-5-thiol.

Substitution of a tetrazole thiol listed above in the procedure of Example 5 in place of 1-carbamoylmethyltetrazole-5-thiol gives the cephalosporin compounds of this invention listed below:

7-D-mandelamido-3-[1-(2-carbamoyl-1-methylethyl)-tetrazol-5-ylthiomethyl]-3-cephem-4-carboxylic acid
7-D-mandelamido-3-[1-(1-carbamoylethyl)tetrazol-5-ylthiomethyl]-3-cephem-4-carboxylic acid
7-D-mandelamido-3-[1-(1-carbamoylpropyl)tetrazol-5-ylthiomethyl]-3-cephem-4-carboxylic acid
7-D-mandelamido-3-[1-(1-carbamoylbutyl)tetrazol-5-ylthiomethyl]-3-cephem-4-carboxylic acid
7-D-mandelamido-3-[1-(1-carbamoylpentyl)tetrazol-5-ylthiomethyl]-3-cephem-4-carboxylic acid.

In a similar manner, 7-amino-, 7-(D-α-amino-4-hydroxyphenylacetamido)- and 7-trifluoromethylmercaptoacetamido-3-(carbamoylalkyltetrazol-5-ylthiomethyl)-3-cephem-4-carboxylic acids are prepared from a substituted tetrazole thiol listed above and 7-aminocephalosporanic acid, 7-(D-α-t-butoxycarbonyl-4-hydroxyphenylacetamido)cephalosporanic acid and 7-trifluoromethylmercaptoacetamidocephalosporanic acid, respectively, with removal of the protective groups when necessary as previously described.

EXAMPLE 24

Reaction of the t-butoxycarbonyl derivative of the following cephalosporanic acids:

7-(α-amino-4-formamidophenylacetamido)cephalosporanic acid
7-(α-amino-3-formamidophenylacetamido)cephalosporanic acid
7-(α-amino-4-ureidophenylacetamido)cephalosporanic acid
7-(α-amino-3-ureidophenylacetamido)cephalosporanic acid
7-(α-amino-4-hydroxymethylphenylacetamido)cephalosporanic acid
7-(α-amino-1,4-cyclohexadienylacetamido)cephalosporanic acid
7-(α-amino-3-fluoro-4-hydroxyphenylacetamido)cephalosporanic acid with 1-(2-carbamoylethyl)tetrazole-5-thiol as described in the procedure of Example 2 followed by removal of the protective group as described therein gives the following compounds:

7-(α-amino-4-formamidophenylacetamido)-3-[1-(2-carbamoylethyl)tetrazol-5-ylthiomethyl]-3-cephem-4-carboxylic acid
7-(α-amino-3-formamidophenylacetamido)-3-[1-(2-carbamoylethyl)tetrazol-5-ylthiomethyl]-3-cephem-4-carboxylic acid
7-(α-amino-4-ureidophenylacetamido)-3-[1-(2-carbamoylethyl)tetrazol-5-ylthiomethyl]-3-cephem-4-carboxylic acid
7-(α-amino-3-ureidophenylacetamido)-3-[1-(2-carbamoylethyl)tetrazol-5-ylthiomethyl]-3-cephem-4-carboxylic acid
7-(α-amino-4-hydroxymethylphenylacetamido)-3-[1-(2-carbamoylethyl)tetrazol-5-ylthiomethyl]-3-cepehm-4-carboxylic acid
7-(α-amino-1,4-cyclohexadienylacetamido)-3-[1-(2-carbamoylethyl)tetrazol-5-ylthiomethyl]-3-cephem-4-carboxylic acid
7-(α-amino-3-fluoro-4-hydroxyphenylacetamido)-3-[1-(2-carbamoylethyl)tetrazol-5-ylthiomethyl]-3-cephem-4-carboxylic acid.

By similar procedures described hereinabove, 7-(α-amino substituted phenylacetamido)-3-[1-(2-carboxyethyl)tetrazol-5-ylthiomethyl]-3-cephem-4-carboxylic acids are prepared by reaction of the t-butoxycarbonyl derivative of the cephalosporanic acids listed above with 1-(2-carboxyethyl)tetrazole-5-thiol followed by removal of the protective group as previously described.

EXAMPLE 25

7-(4-Hydroxymandelamido)-3-[1-(2-carbamoylethyl)tetrazol-5-ylthiomethyl]-3-cephem-4-carboxylic acid is prepared by reaction of 7-(4-hydroxymandelamido)cephalosporanic acid sodium salt and 1-(2-carbamoylethyl)tetrazole-5-thiol as described in the procedure of Example 1.

Likewise, when 7-(4-hydroxymandelamido)cephalosporanic acid sodium salt and 1-(2-carboxyethyl)tetrazole-5-thiol are substituted in the procedure of Example 1 for 7-D-mandelamidocephalosporanic acid sodium salt and 1-carboxymethyltetrazole-5-thiol, 7-(4-hydroxymandelamido)-3-[1-(2-carboxyethyl)tetrazol-5-ylthiomethyl]-3-cephem-4-carboxylic acid is obtained.

EXAMPLE 26

Reaction of a cephalosporanic acid listed below:
7-(α-hydroxythienylacetamido)cephalosporanic acid
7-(α-carboxythienylacetamido)cephalosporanic acid
7-(α-sulphophenylacetamido)cephalosporanic acid
with 1-(2-carbamoylethyl)tetrazole-5-thiol or 1-(2-carboxyethyl)tetrazole-5-thiol as described in the procedure of Example 2 gives the following compounds of this invention:

- 7-(α-hydroxythienylacetamido)-3-[1-(2-carbamoylethyl)tetrazol-5-ylthiomethyl]-3-cephem-4-carboxylic acid
- 7-(α-hydroxythienylacetamido)-3-[1-(2-carboxyethyl)tetrazol-5-ylthiomethyl]-3-cephem-4-carboxylic acid
- 7-(α-carboxythienylacetamido)-3-[1-(2-carbamoylethyl)tetrazol-5-ylthiomethyl]-3-cephem-4-carboxylic acid
- 7-(α-carboxythienylacetamido)-3-[1-(2-carboxyethyl)tetrazol-5-ylthiomethyl]-3-cephem-4-carboxylic acid
- 7-(α-sulphophenylacetamido)-3-[1-(2-carbamoylethyl)tetrazol-5-ylthiomethyl]-3-cephem-4-carboxylic acid
- 7-(α-sulphophenylacetamido)-3-[1-(2-carboxyethyl)tetrazol-5-ylthiomethyl]-3-cephem-4-carboxylic acid.

EXAMPLE 27

When the t-butoxycarbonyl derivative of 7-(α-aminothienylacetamido)cephalosporanic acid is reacted with 1-(2-carbamoylethyl)tetrazole-5-thiol or 1-(2-carboxyethyl)tetrazole-5-thiol according to the procedure of Example 2 followed by removal of the protective groups as described above, 7-(α-aminothienylacetamido)-3-[1-(2-carbamoylethyl)tetrazol-5-ylthiomethyl]-3-cephem-4-carboxylic acid and 7-(α-aminothienylacetamido)-3-[1-(2-carboxyethyl)tetrazol-5-ylthiomethyl]-3-cephem-4-carboxylic acid are obtained, respectively.

EXAMPLE 28

A mixture of 2.5 g. (7.7 mmol.) of D-α-(N-t-butoxycarbonyl)-4-aminophenylglycine, 1.8 g. (9.2 mmol.) of α-bromoacetic acid t-butyl ester and 2.5 g. (19.2 mmol.) of diisopropyl ethylamine in 15 ml. of ethanol was stirred at 25° for 48 hours. The solvent was removed in vacuo, the residue was diluted with ethyl acetate and sodium bicarbonate and the pH was adjusted to 2.5. The layers were separated and the aqueous phase was again extracted with ethyl acetate. The combined extracts were washed with saturated sodium chloride solution, dried (MgSO$_4$) and evaporated to dryness to give D-α-(N-t-butoxycarbonyl)-4-t-butoxycarbonylmethylaminophenylglycine.

A solution of 0.380 g. (1.0 mmol.) of D-α-(N-t-butoxycarbonyl)-4-t-butoxycarbonylmethylaminophenylglycine, 0.296 g. (1.0 mmol.) of 7-aminocephalosporanic acid t-butyl ester and 0.210 g. (1.0 mmol.) of dicyclohexylcarbodiimide in 25 ml. of 9:1 ethyl acetate-methylene chloride was stirred at 0° for one hour. The reaction mixture was filtered and the filtrate was washed with 2.5% sulfuric acid, 5% sodium bicarbonate and water, dried (MgSO$_4$) and evaporated to dryness to give 7-(D-α-t-butoxycarbonylamino-4-carboxymethylaminophenylacetamido)cephalosporanic acid t-butyl ester. Deblocking was accomplished by stirring a mixture of the cephalosporanic acid t-butyl ester and 2 ml. of benzenethio in 10 ml. of trifluoroacetic acid at 25° for one hour. Evaporation of the reaction mixture to dryness gave 7-(D-α-amino-4-carboxymethylaminophenylacetamido)cephalosporanic acid.

Reaction of the t-butoxycarbonyl derivative of 7-(D-α-amino-4-carboxymethylaminophenylacetamido)cephalosporanic acid with 1-(2-carbamoylethyl)tetrazole-5-thiol or 1-(2-carboxyethyl)tetrazole-5-thiol according to the procedure of Example 2 with subsequent removal of the protective group as described above gives 7-(D-α-amino-4-carboxymethylaminophenylacetamido)-3-[1-(2-carbamoylethyl)tetrazol-5-ylthiomethyl]-3-cephem-4-carboxylic acid and 7-(D-α-amino-4-carboxymethylaminophenylacetamido)-3-[1-(2-carboxyethyl)tetrazol-5-ylthiomethyl]-3-cephem-4-carboxylic acid, respectively.

EXAMPLE 29

When ethylamine, propylamine or butylamine is reacted with 1-(2-carboxyethyl)tetrazole-5-thiol according to the procedure of Example 3, the following tetrazole thiols are prepared:

1-(2-N-ethylcarbamoylethyl)tetrazole-5-thiol
1-(2-N-propylcarbamoylethyl)tetrazole-5-thiol
1-(2-N-butylcarbamoylethyl)tetrazole-5-thiol.

Reaction of a tetrazole thiol listed above with 7-aminocephalosporanic acid, 7-D-mandelamidocephalosporanic acid, 7-(D-α-t-butoxycarbonylamino-4-hydroxyphenylacetamido)cephalosporanic acid and 7-trifluoromethylmercaptoacetamido-cephalosporanic acid, respectively, with removal of the protective groups when necessary, as described in Example 2, gives the following compounds of this invention:

- 7-amino-3-[1-(2-N-ethylcarbamoylethyl)tetrazol-5-ylthiomethyl]-3-cephem-4-carboxylic acid
- 7-amino-3-[1-(2-N-propylcarbamoylethyl)tetrazol-5-ylthiomethyl]-3-cephem-4-carboxylic acid
- 7-amino-3-[1-(2-N-butylcarbamoylethyl)tetrazol-5-ylthiomethyl]-3-cephem-4-carboxylic acid
- 7-D-mandelamido-3-[1-(2-N-ethylcarbamoylethyl)tetrazol-5-ylthiomethyl]-3-cephem-4-carboxylic acid
- 7-D-mandelamido-3-[1-(2-N-propylcarbamoylethyl)tetrazol-5-ylthiomethyl]-3-cephem-4-carboxylic acid
- 7-D-mandelamido-3-[1-(2-N-butylcarbamoylethyl)tetrazol-5-ylthiomethyl]-3-cephem-4-carboxylic acid
- 7-(D-α-amino-4-hydroxyphenylacetamido)-3-[1-(2-N-ethylcarbamoylethyl)tetrazol-5-ylthiomethyl]-3-cephem-4-carboxylic acid
- 7-(D-α-amino-4-hydroxyphenylacetamido)-3-[1-(2-N-propylcarbamoylethyl)tetrazol-5-ylthiomethyl]-3-cephem-4-carboxylic acid
- 7-(D-α-amino-4-hydroxyphenylacetamido)-3-[1-(2-N-butylcarbamoylethyl)tetrazol-5-ylthiomethyl]-3-cephem-4-carboxylic acid
- 7-trifluoromethylmercaptoacetamido-3-[1-(2-N-ethylcarbamoylethyl)tetrazol-5-ylthiomethyl]-3-cephem-4-carboxylic acid
- 7-trifluoromethylmercaptoacetamido-3-[1-(2-N-propylcarbamoylethyl)tetrazol-5-ylthiomethyl]-3-cephem-4-carboxylic acid
- 7-trifluoromethylmercaptoacetamido-3-[1-(2-N-butylcarbamoylethyl)tetrazol-5-ylthiomethyl]-3-cephem-4-carboxylic acid.

EXAMPLE 30

When diethylamine, dipropylamine or dibutylamine is substituted for dimethylamine in the procedure of Example 4, the following tetrazole thiols are prepared:
1-(2-N,N-diethylcarbamoylethyl)tetrazole-5-thiol
-(2-N,N-dipropylcarbamoylethyl)tetrazole-5-thiol
1-(2-N,N-dibutylcarbamoylethyl)tetrazole-5-thiol.

Reaction of a tetrazole thiol listed above with 7-aminocephalosporanic acid, 7-D-mandelamidocephalosporanic acid, 7-(D-α-t-butoxycarbonylamino-4-hydroxyphenylacetamido)cephalosporanic acid and 7-trifluoromethylmercaptoacetamidocephalosporanic acid, respectively, with removal of the protective groups when necessary, as described in Example 2, gives the following compounds of this invention:
7-amino-3-[1-(2-N,N-diethylcarbamoylethyl)tetrazol-5-ylthiomethyl]-3-cephem-4-carboxylic acid
7-amino-3-[1-(2-N,N-dipropylcarbamoylethyl)tetrazol-5-ylthiomethyl]-3-cephem-4-carboxylic acid
7-amino-3-[1-(2-N,N-dibutylcarbamoylethyl)tetrazol-5-ylthiomethyl]-3-cephem-4-carboxylic acid
7-D-mandelamido-3-[1-(2-N,N-diethylcarbamoylethyl)tetrazol-5-ylthiomethyl]-3-cephem-4-carboxylic acid
7-D-mandelamido-3-[1-(2-N,N-dipropylcarbamoylethyl)tetrazol-5-ylthiomethyl]-3-cephem-4-carboxylic acid
7-D-mandelamido-3-[1-(2-N,N-dibutylcarbamoylethyl)tetrazol-5-ylthiomethyl]-3-cephem-4-carboxylic acid
7-(D-α-amino-4-hydroxyphenylacetamido)-3-[1-(2-N,N-diethylcarbamoylethyl)tetrazol-5-ylthiomethyl]-3-cephem-4-carboxylic acid
7-(D-α-amino-4-hydroxyphenylacetamido)-3-[1-(2-N,N-dipropylcarbamoylethyl)tetrazol-5-ylthiomethyl]-3-cephem-4-carboxylic acid
7-(D-α-amino-4-hydroxyphenylacetamido)-3-[1-(2-N,N-dibutylcarbamoylethyl)tetrazol-5-ylthiomethyl]-3-cephem-4-carboxylic acid
7-trifluoromethylmercaptoacetamido-3-[1-(2-N,N-diethylcarbamoylethyl)tetrazol-5-ylthiomethyl]-3-cephem-4-carboxylic acid
7-trifluoromethylmercaptoacetamido-3-[1-(2-N,N-dipropylcarbamoylethyl)tetrazol-5-ylthiomethyl]-3-cephem-4-carboxylic acid
7-trifluoromethylmercaptoacetamido-3-[1-(2-N,N-dibutylcarbamoylethyl)tetrazol-5-ylthiomethyl]-3-cephem-4-carboxylic acid.

EXAMPLE 31

When a cephalosporanic acid listed below:
7-(3-sydnoneacetamido)cephalosporanic acid
7-cyanoacetamidocephalosporanic acid
7-(2-aminomethylphenylacetamido)cephalosporanic acid
is reacted with 1-(2-carbamoylethyl)tetrazole-5-thiol by the procedure described in Example 2, the following compounds of this invention are obtained, respectively:
7-(3-sydnoneacetamido)-3-[1-(2-carbamoylethyl)tetrazol-5-ylthiomethyl]-3-cephem-4-carboxylic acid
7-cyanoacetamido-3-[1-(2-carbamoylethyl)tetrazol-5-ylthiomethyl]-3-cephem-4-carboxylic acid
7-(2-aminomethylphenylacetamido)-3-[1-(2-carbamoylethyl)tetrazol-5-ylthiomethyl]-3-cephem-4-carboxylic acid.

Similarly, reaction of a cephalosporanic acid listed above with 1-(2-carboxyethyl)tetrazole-5-thiol as described in Example 2 gives the following compounds of this invention:
7-(3-sydnoneacetamido)-3-[1-(2-carboxyethyl)tetrazol-5-ylthiomethyl]-3-cephem-4-carboxylic acid
7-cyanoacetamido-3-[1-(2-carboxyethyl)tetrazol-5-ylthiomethyl]-3-cephem-4-carboxylic acid
7-(2-aminomethylphenylacetamido)-3[1-(2-carboxyethyl)tetrazol-5-ylthiomethyl]-3-cephem-4-carboxylic acid.

EXAMPLE 32

Reaction of a cephalosporanic acid listed below:
7-(2,2,2-trifluoroethylmercaptoacetamido)cephalosporanic acid
7-trifluoromethylsulfinylacetamidocephalosporanic acid
7-(4-pyridylthioacetamido)cephalosporanic acid
7-(3-pyridylthioacetamido)cephalosporanic acid
with 1-(2-carboxyethyl)tetrazole-5-thiol as described in the procedure of Example 15 gives the following compounds of this invention:
7-(2,2,2-trifluoroethylmercaptoacetamido)-3-[1-(2-carboxyethyl)tetrazol-5-ylthiomethyl]-3-cephem-4-carboxylic acid
7-trifluoromethylsulfinylacetamido-3-[1-(2-carboxyethyl)tetrazol-5-ylthiomethyl]-3-cephem-4-carboxylic acid
7-(4-pyridylthioacetamido)-3-[1-(2-carboxyethyl)tetrazol-5-ylthiomethyl]-3-cephem-4-carboxylic acid
7-(3-pyridylthioacetamido)-3-[1-(2-carboxyethyl)tetrazol-5-ylthiomethyl]-3-cephem-4-carboxylic acid.

EXAMPLE 33

Reaction of a cephalosporanic acid listed in Example 32 with 1-(2-carbamoylethyl)tetrazole-5-thiol by the procedure of Example 15 gives the 7-substituted-3-[1-(2-carbamoylethyl)tetrazol-5-ylthiomethyl]-3-cephem-4-carboxylic acids listed below:
7-(2,2,2-trifluoroethylmercaptoacetamido)-3-[1-(2-carbamoylethyl)tetrazol-5-ylthiomethyl]-3-cephem-4-carboxylic acid
7-trifluoromethylsulfinylacetamido-3-[1-(2-carbamoylethyl)tetrazol-5-ylthiomethyl]-3-cephem-4-carboxylic acid
7-(4-pyridylthioacetamido)-3-[1-(2-carbamoylethyl)tetrazol-5-ylthiomethyl]-3-cephem-4-carboxylic acid
7-(3-pyridylthioacetamido)-3-[1-(2-carbamoylethyl)tetrazol-5-ylthiomethyl]-3-cephem-4-carboxylic acid.

EXAMPLE 34

7-(2,2,2-Trifluoroethylsulfinylacetamido)-3-[1-(2-carbamoylethyl)tetrazol-5-ylthiomethyl]-3-cephem-4-carboxylic acid The activated ester of 2,2,2-trifluoroethylsulfinylacetic acid is prepared as described in the procedure of Example 18. Reaction of the activated ester with 7-amino-3-[1-(2-carbamoylethyl)tetrazol-5-ylthiomethyl]-3-cephem-4-carboxylic acid as also described in Example 18 gives the title compound.

In like manner, the 7-(2,2,2-trifluoroethylsulfinylacetamido) derivatives of other 7-amino-3-substituted tetrazole cephalosporins described above may be prepared.

EXAMPLE 35

7-(2,2,2-Trifluoroethylsulfonylacetamido)-3-[1-(2-carbamoylethyl)tetrazol-5-ylthiomethyl]-3-cephem-4-carboxylic acid To a solution of 8.4 g. (0.019 mol.) of 7-amino-3-[1-(2-carbamoylethyl)tetrazol-5-ylthiomethyl]-3-cephem-4-carboxylic acid t-butyl ester and 3.9 g. (0.019 mol.) of 2,2,2-trifluoroethylsulfonylacetic acid in tetrahydrofuran is added dropwise a solution of 3.9 g. (0.019 mol.) of dicyclohexylcarbodiimide in 100 ml. of tetrahydrofuran. The reaction mixture is stirred at 25° for 12 hours, then filtered and concentrated to about 10 ml. The residue is filtered and evaporated to dryness to give 7-(2,2,2-trifluoroethylsulfonylacetmido)-3-[1-(2-carbamoylethyl)tetrazol-5-ylthiomethyl]-3-cephem-4-carboxylic acid t-butyl ester.

The ester is dissolved in acetonitrile and trifluoroacetic acid is added. The solution is stirred for three hours, then evaporated to dryness to give the title compound.

Likewise, 7-(2,2,2-trifluoroethylsulfonylacetamido) derivatives of the other 7-amino-3-substituted tetrazole cephalosporins disclosed herein are prepared.

EXAMPLE 36

7-Methylmercaptoacetamido-3-[1-(2-carbamoylethyl)-tetrazol-5-ylthiomethyl]-3-cephem-4-carboxylic acid To a stirred, cooled (−20°) solution of 10.2 g. (0.026 mol.) of 7-amino-3-[1-(2-carbamoylethyl)tetrazol-5-ylthiomethyl]-3-cephem-4-carboxylic acid in 220 ml. of 3% sodium bicarbonate and 220 ml. of acetone is dropwise added a solution of 3.66 g. (0.029 mol.) of methylmercaptoacetyl chloride in 52 ml. of acetone, during which time the pH of the reaction mixture is maintained at 8.0 by addition of 10% sodium hydroxide. After addition the reaction mixture is stirred an additional 20 minutes at −15°, then is warmed to 25° and extracted with ether. The remaining aqueous phase is cooled, 250 ml. of ethyl acetate is added and the slurry is acidified with 3N hydrochloric acid. The layers are separated and the aqueous phase is extracted twice more with ethyl acetate. The combined extracts are dried (MgSO₄) and evaporated to dryness to yield the title compound.

EXAMPLE 37

7-n-Propylmercaptoacetamido-3-[1-(2carbamoylethyl)-tetrazol-5-ylthiomethyl]-3-cephem-4-carboxylic acid The title compound is prepared by substitution of n-propylmercaptoacetyl chloride in the procedure of Example 36 for methylmercaptoacetyl chloride.

In a similar manner, other 7-alkylmercaptoacetamido-3-substituted tetrazole cephalosporins of this invention are prepared from the appropriate 7-alkylmercaptoacetyl chloride and 7-amino-3-(substituted tetrazol-5-ylthiomethyl)-3-cephem-4-carboxylic acid.

EXAMPLE 38

7-(α-Carboxythienylacetamido)-3-(1-carboxymethyltetrazol-5-ylthiomethyl)-3-cephem-4-carboxylic acid (XIX)

7-Amino-3-(1-carboxymethyltetrazol-5-ylthiomethyl)-3-cephem-4-carboxylic acid was prepared as described in Example 17 from reaction of 1-carboxymethyltetrazole-5-thiol and 7-aminocephalosporanic acid.

7-Amino-3-(1-carboxymethyltetrazol-5-ylthiomethyl)-3-cephem-4-carboxylic acid (1.0 g., 2.68 mmol.) was suspended in 10 ml. of dry dimethylformamide and 1.12 ml of triethylamine was added followed by 85 drops of formamide. A solution of 0.91 g. (2.68 mmol.) of the activated ester of α-t-butoxycarbonylthienylacetamide, prepared as described above, in 2 ml. of dimethylformamide was added and the reaction mixture was stirred at 25° for three hours. An additional 0.45 g. of activated ester was then added and the mixture stirred another five hours. Ether (ca. 300 ml.) was added and the solution was decanted. The remaining oily material was washed with ether, dissolved in water and the aqueous solution was extracted with ethyl acetate. The pH of the ethyl acetate solution was adjusted to 1.5 by addition of dilute hydrochloric acid. Extraction with ethyl acetate and evaporation of the solvent gave 7-(α-t-butoxycarbonylthienylacetamido)-3-(1-carboxymethyltetrazol-5-ylthiomethyl)-3-cephem-4-carboxylic acid.

7-(α-t-Butoxycarbonylthienylacetamido)-3-(1-carboxymethyltetrazol-5-ylthiomethyl)-3-cephem-4-carboxylic acid (0.8 g.) was dissolved in a mixture of 10 ml. of trifluoroacetic acid and 10 ml. of m-dimethoxybenzene and stirred at 25° for one hour. Ether was added and the precipitate was collected and dissolved in 50 ml. of ethyl acetate. Addition of sodium 2-ethylhexanoate gave 7-(α-carboxythienylacetamido)-3-(1-carboxymethyltetrazol-5-ylthiomethyl)-3-cephem-4-carboxylic acid trisodium salt.

$C_{18}H_{13}N_6O_8S_3.2.5$ Na.2 $H_2O.0.15 C_4H_8O_2$— Calculated: 34.62% C; 2.92% H; 13.02% N. Found: 35.34% C; 3.03% H; 12.26% N.

The salt was converted to the title compound as previously described.

EXAMPLE 39

When 7-aminoheptanoic acid or 9-aminononanoic acid is substituted in the procedure of Example 19 in place of 11-aminoundecanoic acid and the resulting methyl carboxydithiocarbamate is treated with sodium azide as described therein, 1-(6-carboxyhexyl)tetrazole-5-thiol and 1-(8-carboxyoctyl)tetrazole-5-thiol are obtained, respectively.

Reaction of 1-(6-carboxyhexyl)tetrazole-5-thiol and 1-(8-carboxyoctyl)tetrazole-5-thiol with 7-D-mandelamidocephalosporanic acid as described in Example 19 gives 7-D-mandelamido-3-[1-(6-carboxyhexyl)tetrazol-5-ylthiomethyl]-3-cephem-4-carboxylic acid and 7-D-mandelamido-3-[1-(8-carboxyoctyl)tetrazol-5-ylthiomethyl]-3-cephem-4-carboxylic acid, respectively.

EXAMPLE 40

1-(6-Carbamoylhexyl)tetrazole-5-thiol and 1-(8-carbamoyloctyl)tetrazole-5-thiol are prepared from 1-(6-carboxyhexyl)tetrazole-5-thiol and 1-(8-carboxyoctyl)tetrazole-5-thiol according to the procedure described in Example 5.

Reaction of 1-(6-carbamoylhexyl)tetrazole-5-thiol and 1-(8-carbamoyloctyl)tetrazole-5-thiol with 7-D-mandelamidocephalosporanic acid as described in Example 19 gives, respectively, 7-D-mandelamido-3-[1-(6-carbamoylhexyl)tetrazol-5-ylthiomethyl]-3-cephem-4-carboxylic acid and 7-D-mandelamido-3-[1-(8-carbamoyloctyl)tetrazol-5-ylthiomethyl]-3-cephem-4-carboxylic acid.

EXAMPLE 41

7-Trifluoromethylmercaptoacetamido-3-(1-carboxymethyltetrazol-5-ylthiomethyl)-3-cephem-4-carboxylic acid (XVIII)

Reaction of 0.96 g. (6 mmol.) of 1-carboxymethyltetrazole-5-thiol and 1.74 g. (4 mmol.) of 7-trifluoromethylmercaptoacetamidocephalosporanic acid as described in the procedure of Example 15 gave the title compound as the corresponding disodium salt.

The disodium salt was converted to the title compound as previously described. The title compound was dissolved in ethyl acetate and cyclohexylamine and methanol were added to the solution. The mixture was evaporated under reduced pressure to give the cyclohexylamine salt of the title compound.

$C_{13}H_{11}F_3N_6S_3O_6 \cdot C_6H_{13}N$—Calculated: 39.15% C; 4.27% H; 15.98% N. Found: 39.36% C; 4.30% H; 15.75% N.

Example 42

7-Trifluoromethylmercaptoacetamido-3-[1-(3-carbamoylpropyl)tetrazol-5-ylthiomethyl]-3-cephem-4-carboxylic acid (XX)

Reaction of 2.81 g. (15 mmol.) of 1-(3-carbamoylpropyl)tetrazole-5-thiol, 4.52 g. (10 mmol.) of 7-trifluoromethylmercaptoacetamidocephalosporanic acid and 1.27 g. (15 mmol.) of sodium bicarbonate according to the procedure described in Example 15 gave the title compound as its sodium salt.

$C_{16}H_{17}F_3N_7O_5S_3 \cdot Na \cdot 0.75H_2O$— Calculated: 33.30% C; 3.23% H; 16.99% N. Found: 33.59% C; 3.50% H; 16.44% N.

7-Trifluoromethylmercaptoacetamido-3-[1-(3-carbamoylpropyl)tetrazol-5-ylthiomethyl]-3-cephem-4-carboxylic acid sodium salt was converted to the title compound as described in Example 15.

EXAMPLE 43

7$\beta$-Cyanoacetamido-7$\alpha$-methoxy-3-[1-(2-carboxyethyl)tetrazol-5-ylthiomethyl]-3-cephem-4-carboxylic acid To a suspension of 19.3 g. (0.05 mol.) of 7-amino-3-[1-(2-carboxyethyl)tetrazol-5-ylthiomethyl]-3-cephem-4-carboxylic acid in 500 ml. of methylene chloride was added over a 30 minute interval a solution of 60.0 g. (0.3 mol.) of O-t-butyldiisopropylpseudourea in 100 ml. of methylene chloride. The mixture was stirred at ambient temperature for 72 hours. The precipitate was removed by filtration and the filtrate was evaporated to a residue which was taken up in 200 ml. of benzene and filtered again. The filtrate was extracted with three 100 ml. portions of cold 1N hydrochloric acid. The aqueous extracts were layered with ethyl acetate and the pH was adjusted to 7.5 by addition of solid sodium bicarbonate. The organic layer was separated and the aqueous phase extracted with two 150 ml. portions of ethyl acetate. The combined extracts were dried (MgSO$_4$), filtered and evaporated to dryness to give 6.1 g. of 7-amino-3-[1-(2-t-butoxycarbonylethyl)tetrazol-5-ylthiomethyl]-3-cephem-4-carboxylic acid t-butyl ester.

A solution of 1.19 g. (2.4 mmol.) of 7-amino-3-[1-(2-t-butoxycarbonylethyl)tetrazol-5-ylthiomethyl]-3-cephem 4-carboxylic acid t-butyl ester and 0.56 g. (2.4 mmol.) of 3,5-di-t-butyl-4-hydroxybenzaldehyde in 100 ml. of dry benzene was refluxed for 4 hours under a Dean-Stark trap. The solution was evaporated under reduced pressure to leave a residue which was dissolved in 100 ml. of 1,2-dichloroethane and cooled to ca. 5° in an ice bath. Three grams of freshly prepared lead dioxide was added in portions over 20 minutes until the starting material was completely consumed. The mixture was filtered through Celite and the filter cake was washed with two 20 ml. portions of cold 1,2-dichloroethane. The filtrate was treated with 25 ml. of methanol (distilled from magnesium) and the reaction mixture was allowed to stand at room temperature until complete consumption of the oxidized intermediate and formation of a new slower-moving product was shown by thin layer chromatography (ca. 3 hours). The mixture was evaporated to yield a brown semi-solid which was dissolved in 30 ml. of methanol and treated with 2.5 g. of Girard reagent T (trimethylaminoacetohydrazide chloride). The reaction mixture was stirred at room temperature for 3 hours, then evaporated to give a solid residue which was partitioned between 100 ml. of ethyl acetate and 100 ml. of 20% sodium chloride solution. The organic phase was washed with three 100 ml. portions of 10% sodium chloride solution, two 100 ml. portions of water and 100 ml. of a saturated sodium chloride solution. The organic phase was dried (MgSO$_4$), filtered and evaporated to dryness to give 7$\beta$-amino-7$\alpha$-methoxy-3-[1-(2-t-butoxycarbonylethyl)-tetrazol-5-ylthiomethyl]-3-cephem-4-carboxylic acid t-butyl ester.

A solution of 2.11 g. (4 mmol.) of 7$\beta$-amino-7$\alpha$-methoxy-3-[1-(2-t-butoxycarbonylethyl)tetrazol-5-ylthiomethyl]-3-cephem-4-carboxylic acid t-butyl ester and 0.60 g. (4 mmol.) of N,N-diethylaniline in 100 ml. of dry methylene chloride is stirred at 0°–5° while 0.41 g. (4 mmol.) of cyanoacetyl chloride in 20 ml. of methylene chloride is added over a 10 minute period. The mixture is stirred in the cold for 30 minutes and then at ambient temperature for an additional 30 minutes. The reaction mixture is washed with 100 ml. of dilute hydrochloric acid, 100 ml. of 5% sodium bicarbonate and water. The organic phase is dried and evaporated to give a gum which is dissolved in 20 ml. of 2:1 trifluoroacetic acid-m-dimethoxybenzene and stirred for 3 hours. Excess trifluoroacetic acid is evaporated and the residue is added to 200 ml. of rapidly stirred ether. The resulting precipitate is collected, washed well with ether and dried to give the title compound.

EXAMPLE 44

7$\beta$-(D-$\alpha$-aminophenylacetamido)-7$\alpha$-methoxy-3-[1-(2-carboxyethyl)tetrazol-5-ylthiomethyl]-3-cephem-4-carboxylic acid To a solution of 2.11 g. (4 mmol.) of 7$\beta$-amino-7$\alpha$-methoxy-3-[1-(2-t-butoxycarbonylethyl)tetrazol-5-ylthiomethyl]-3-cephem-4-carboxylic acid t-butyl ester and 1.00 g. (4 mmol.) of D-$\alpha$-(N-t-butoxycarbonyl)-phenylglycine in 50 ml. of dry tetrahydrofuran is added 0.82 g. (4 mmol.) of dicyclohexylcarbodiimide. The mixture is stirred at ambient temperature for 3 hours. The precipitated urea is removed by filtration and the solvent is evaporated to leave a residue which is taken up in 100 ml. of chloroform and washed with 100 ml. portions of dilute hydrochloric acid, 5% aqueous sodium bicarbonate and water. The organic layer is separated, dried and evaporated to give a residue which is dissolved in 20 ml. of 2:1 trifluoroacetic acid-m-dimethoxybenzene and stirred for 3 hours. Excess trifluoroacetic acid is evaporated under vacuum and the residue is added dropwise to 300 ml. of rapidly stirred ether. The precipicate is removed by filtration, washed with ether and dried to give the title compound as its trifluoroacetic acid salt.

An aqueous solution of the trifluoroacetic acid salt is brought to pH 5.0 by addition of dilute aqueous sodium hydroxide. After lyophilization, the lyophilized material is dissolved in methanol and ether is added to precipitate 7β-(D-α-aminophenylacetamido)-7α-methoxy-3-[1-(2-carboxyethyl)tetrazol-5-ylthiomethyl]-3-cephem-4-carboxylic acid disodium salt. This salt is dissolved in water and the aqueous solution is passed through an Amberlite IR-50 ion exchange resin column. Lyophilization of the eluted material gives the title compound.

EXAMPLE 45

7β-D-Mandelamido-7α-methoxy-3-[1-(2-carboxyethyl)tetrazol-5-ylthiomethyl]-3-cephem-4-carboxylic acid A solution of 1.06 g. (2 mmol.) of 7β-amino-7α-methoxy-3-[1-(2-t-butoxycarbonylethyl)tetrazol-5-ylthiomethyl]-3-cephem-4-carboxylic acid t-butyl ester and 0.30 g. (2 mmol.) of N,N-diethylaniline in 100 ml. of dry methylene chloride is stirred at 0°–5° while 0.56 g. (2 mmol.) of D-O-dichloroacetylmandeloyl chloride in 10 ml. of methylene chloride is added dropwise over 10 minutes. The mixture is stirred in the cold for 30 minutes then warmed to room temperature and stirred for an additional 30 minutes. The solution is washed with 50 ml. of cold dilute hydrochloric acid and 50 ml. of cold 5% aqueous sodium bicarbonate, dried and evaporated to dryness. The residue is dissolved in a mixture of 10 ml. of trifluoroacetic acid and 2 ml. of m-dmethoxybenzene and stirred at ambient temperature for 2 hours. The excess trifluoroacetic acid is evaporated under vacuum and the residue is partitioned between 50 ml. of ether and 50 ml. of water and adjusted to pH 9.3–9.5 with 5% aqueous sodium carbonate. The organic phase is separated and discarded. The aqueous phase is stirred at pH 9.3–9.5 for 30 minutes, extracted with 50 ml. of ethyl acetate which is discarded, layered with fresh ethyl acetate and adjusted to pH 1.5 with dilute hydrochloric acid. The aqueous layer is extracted with three 50 ml. portions of ethyl acetate and the combined extracts are dried and evaporated to a small volume. Petroleum ether is added dropwise to precipitate the title compound which is collected by filtration and dried.

EXAMPLE 46

7β-D-Mandelamido-7α-methoxy-3-[1-(2-carbamoylethyl)tetrazol-5-ylthiomethyl]-3-cephem-4-carboxylic acid To a suspension of 19.3 g. (0.05 mol.) of 7-amino-3-[1-(2-carbamoylethyl)tetrazol-5-ylthiomethyl]-3-cephem-4-carboxylic acid in 500 ml. of dry methylene chloride is added in one portion 30.0 g. (0.15 mol.) of O-t-butyldiisopropylpseudourea in 50 ml. of methylene chloride and the mixture is stirred at ambient temperature for 24 hours. The precipitate is removed by filtration and the filtrate is evaporated to give a residue which is taken up in 200 ml. of benzene and filtered again. The filtrate is extracted with three 100 ml. portions of cold 1N hydrochloric acid. The aqueous extracts are layered with ethyl acetate and the pH is adjusted to 7.5 by addition of solid sodium bicarbonate. The organic layer is separated and the aqueous phase is extracted with two 150 ml. portions of ethyl acetate. The combined extracts are dried (MgSO₄), filtered and evaporated to dryness to give 7-amino-3-[1-(2-carbamoylethyl)tetrazol-5-ylthiomethyl]-3-cephem-4-carboxylic acid t-butyl ester.

A solution of 1.76 g. (4 mmol.) of 7-amino-3-[1-(2-carbamoylethyl)tetrazol-5-ylthiomethyl]-3-cephem-4-carboxylic acid t-butyl ester and 0.94 g. (4 mmol.) of 3,5-di-t-butyl-4-hydroxybenzaldehyde in 150 ml. of dry benzene is refluxed for ca. 4 hours under a Dean-Stark trap until no more water separates. The solution is evaporated uner reduced pressure to give a residue which is dissolved in 150 ml. of 1,2-dichloroethane and cooled to 0°–5° in an ice bath. Freshly prepared lead dioxide (5 g.) is added in 1 g. portions over 30 minutes and the reaction is stirred in the cold until complete consumption of starting material is shown by thin layer chromatography. The mixture is then filtered through Celite and the filter cake is washed with two 30 ml. portions of cold 1,2-dichloroethane. The filtrate is treated with 30 ml. of dry methanol (distilled from magnesium) and the reaction mixture is stirred at ambient temperature until complete consumption of the intermediate and formation of a new product are shown by thin layer chromatography. The reaction mixture is evaporated to dryness and the residue is taken up in 50 m. of methanol and treated with 4.0 g. of Girard reagent T. This solution is stirred at ambient temperature for 3 hours, evaporated under vacuum to a solid residue and partitioned between 150 ml. of ethyl acetate and 100 ml. of 20% aqueous sodium chloride solution. The organic phase is washed with three 100 ml. portions of 10% aqueous sodium chloride, two 100 ml. portions of water and 100 ml. of a saturated sodium chloride solution. The organic phase is dried (MgSO₄), filtered and evaporated to dryness to give 7β-amino-7α-methoxy-3-[1-(2-carbamoylethyl)tetrazol-5-ylthiomethyl]-3-cephem-4-carboxylic acid t-butyl ester.

Reaction of 7β-amino-7α-methoxy-3-[1-(2-carbamoylethyl)tetrazol-5-ylthiomethyl]-3-cephem-4-carboxylic acid t-butyl ester with D-O-dichloroacetylmandeloyl chloride as described in the procedure of Example 45 gives the title compound.

EXAMPLE 47

An injectable pharmaceutical composition is formed by adding sterile water or sterile saline solution (2 ml.) to 500 mg. of 7-D-mandelamido-3-[1-(2-carbamoylethyl)tetrazol-5-ylthiomethyl]-b 3-cephem-4-carboxylic acid sodium salt.

Pharmaceutical compositions of the other antibacterial compounds disclosed above may be formulated in a similar manner.

EXAMPLE 48

A tablet or capsule is formed from 500 mg. of 7-tri fluoromethylmercaptoacetamido-3-(1-carbamoylmethyltetrazol-5-ylthiomethyl)-3-cephem-4-carboxylic acid, 250 mg. of lactose and 75 mg. of magnesium stearate.

Tablets or capsules of the other antibacterial compounds disclosed above may be formulated in a similar manner.

What is claimed is:
1. A compound of the formula:

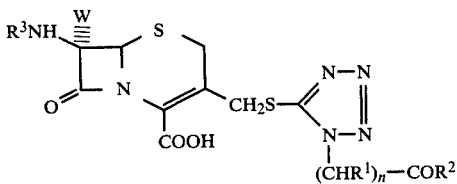

in which:
 each individual $R^1$ is hydrogen or lower alkyl of from one to four carbon atoms;
 n is one to ten;
 $R^2$ is hydroxy, amino, lower alkylamino or di(lower-)alkylamino, each alkyl having from one to four carbon atoms;
 W is hydrogen or methoxy; and
 $R^3$ is an acyl group of the formula:

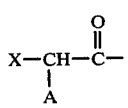

where:
 X is thienyl; dihydrophenyl; phenyl; phenyl monosubstituted with hydroxy, hydroxymethyl, formamido, ureido or carboxymethylamino; or 3-fluoro-4-hydroxyphenyl; and
 A is $NH_2$, OH, COOH or $SO_3H$ provided that A is not $NH_2$ or OH when $R^2$ is hydroxy,
or a non-toxic pharmaceutically acceptable salt thereof.

2. A compound according to claim 1 in which W is hydrogen.

3. A compound according to claim 1 in which W is methoxy.

4. A compound according to claim 2 in which A is $NH_2$.

5. A compound according to claim 2 in which A is OH.

6. A compound according to claim 2 in which A is COOH.

7. A compound according to claim 2 in which A is $SO_3H$.

8. A compound according to claim 2 in which $R^1$ is hydrogen and n is one to five.

9. A compound according to claim 3 in which $R^1$ is hydrogen and n is one to five.

10. A compound according to claim 8 in which $R^2$ is amino and X is phenyl or 4-hydroxyphenyl.

11. A compound according to claim 10, said compound being 7-mandelamido-3-(1-carbamoylmethyltetrazol-5-ylthiomethyl)-3-cephem-4-carboxylic acid.

12. A compound according to claim 10, said compound being 7-mandelamido-3-[1-(2-carbamoylethyl)-tetrazol-5-ylthiomethyl]-3-cephem-4-carboxylic acid.

13. A compound according to claim 10, said compound being 7-mandelamido-3-[1-(3-carbamoylpropyl)-tetrazol-5-ylthiomethyl]-3-cephem-4-carboxylic acid.

14. A compound according to claim 10, said compound being 7-mandelamido-3-[1-(5-carbamoylpentyl)-tetrazol-5-ylthiomethyl]-3-cephem-4-carboxylic acid.

15. A compound according to claim 10, said compound being 7-($\alpha$-amino-4-hydroxyphenylacetamido)-3-(1-carbamoylmethyltetrazol-5-ylthiomethyl)-3-cephem-4-carboxylic acid.

16. A compound according to claim 9, said compound being 7$\beta$-mandelamido-7$\alpha$-methoxy-3-[1-(2-carbamoylethyl)tetrazol-5-ylthiomethyl]-3-cephem-4-carboxylic acid.

17. A pharmaceutical composition having antibacterial activity comprising a compound as claimed in claim 1 and a pharmaceutically acceptable carrier therefor.

18. A pharmaceutical composition having antibacterial activity comprising a compound as claimed in claim 12 and a pharmaceutically acceptable carrier therefor.

19. A method of treating bacterial infections comprising administering internally either orally or by injection to an infected or susceptible warm-blooded animal an antibacterially effective but nontoxic dose of a compound as claimed in claim 1.

20. A method as claimed in claim 19, in which the compound is 7-mandelamido-3-[1-(2-carbamoylethyl)-tetrazol-5-ylthiomethyl]-3-cephem-4-carboxylic acid.

21. A compound of the formula:

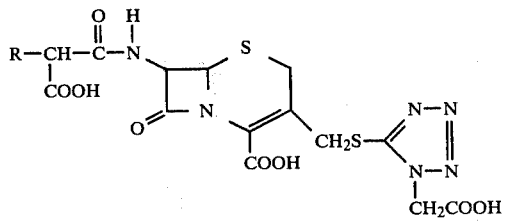

in which:
 R is thienyl, phenyl, hydroxyphenyl,
 3-halo-4-hydroxyphenyl or dihydrophenyl,
or a non-toxic pharmaceutically acceptable salt or ester thereof.

* * * * *